United States Patent [19]
Youdim et al.

[11] Patent Number: 5,576,353
[45] Date of Patent: Nov. 19, 1996

[54] METHOD OF TREATING MEMORY DISORDERS USING R-ENANTIOMERS OF N-PROPARGYL-AMINOINDAN COMPOUNDS

[75] Inventors: Moussa B. H. Youdim, Haifa; John P. M. Finberg, Tivon; Ruth Levy, Tel-Aviv; Haim Yellin, Ramat-Gan, all of Israel

[73] Assignees: Teva Pharmaceutical Industries Ltd., Jerusalem; Technion Research and Development Foundation, Ltd., Haifa, both of Israel

[21] Appl. No.: 459,402

[22] Filed: Jun. 2, 1995

Related U.S. Application Data

[62] Division of Ser. No. 198,205, Feb. 17, 1994, Pat. No. 5,457,133, which is a continuation of Ser. No. 63,461, May 18, 1993, abandoned, which is a continuation of Ser. No. 632,184, Dec. 21, 1990, abandoned.

[30] Foreign Application Priority Data

Jan. 3, 1990 [IL] Israel .......................... 92952

[51] Int. Cl.$^6$ .................................. A61K 31/135
[52] U.S. Cl. .................. 514/647; 564/308; 514/567; 514/614
[58] Field of Search .................. 514/647, 567, 514/614; 564/308

[56] References Cited

U.S. PATENT DOCUMENTS

| | | | |
|---|---|---|---|
| 3,201,470 | 8/1965 | Huebner | 260/577 |
| 3,253,037 | 5/1966 | Huebner | 260/577 |
| 3,513,244 | 5/1970 | Gittos et al. | 424/320 |
| 4,826,875 | 5/1989 | Chiesi | 514/534 |
| 5,196,583 | 3/1993 | Yamada et al. | 564/305 |

FOREIGN PATENT DOCUMENTS 1003686  9/1965  United Kingdom .

OTHER PUBLICATIONS

Finberg and Youdim, *British J. Pharmac.* (Jun. 1985) 85(2):541–546;.
Kabins and Gershon, *Demetia* (1990) 1:323–348;.
The Merck Index (Tenth ed. 1983) pp. 149, 248–249;.
The Parkinson Study Group, *New England J. Med.* (1989) 321(20):1364–1371;.
The Parkinson Study Group, *New England J. Med.* (Jan. 21, 1993) 328(3):176–183;.
Riederer and Youdim, *J. Neurochem.* (1986) 46(5):1359–1365;.
Tekes, et al., *Pol. J. Pharmacol. Pharm.* (1988) 40:653–658;.
Youdim, et al., in Handbook of Experimental Pharmacology vol. 90/I (1988) Chapter 3, Trendelenburg and Weiner, eds.

*Primary Examiner*—Brian M. Burn
*Attorney, Agent, or Firm*—John P. White

[57] ABSTRACT

R(+)-N-propargyl-1-aminoindan, its preparation and use and pharmaceutical compositions containing it. The novel compound was found to be useful for the treatment of human patients for Parkinson's disease, memory disorders, dementia of the Alzheimer type (DAT), depression and the hyperactive syndrome.

7 Claims, 17 Drawing Sheets

METHOD OF TREATING MEMORY DISORDERS USING R-ENANTIOMERS OF N-PROPARGYL-AMINOINDAN COMPOUNDS

This is a divisional of U.S. Ser. No. 08/198,205 filed Feb. 17, 1994 (now U.S. Pat. No. 5,457,133), which is a continuation of U.S. Ser. No. 08/063,461, filed May 18, 1993, now abandoned, which is a continuation of U.S. Ser. No. 07/632,184, filed Dec. 21, 1990, now abandoned, claiming priority of Israeli Patent Application No. 92,952, filed Jan. 3, 1990, the contents of which are hereby incorporated by reference.

FIELD OF THE INVENTION

The present invention is in the field of selective irreversible inhibitors of the enzyme monoamine oxidase (hereinafter MAO) and relates to the R(+) enantiomer of N-propargyl-1-aminoindan (hereinafter, PAI) which is a selective irreversible inhibitor of the B-form of the monoamine oxidase enzyme (hereinafter, MAO-B). The invention also relates to pharmaceutical compositions containing R(+) PAI which is particularly useful for the treatment of Parkinson's disease, memory disorders and dementia of the Alzheimer type (DAT), depression, and hyperactive syndrome in children.

BACKGROUND OF THE INVENTION AND PRIOR ART

Parkinson's disease is widely considered to be the result of degradation of the pre-synaptic dopaminergic neurons in the brain, with a subsequent decrease in the amount of the neurotransmitter dopamine, that is being released. Inadequate dopamine release, therefore, leads to the onset of voluntary muscle control disturbances symptomatic of Parkinson's disease.

Various procedures for treating Parkinson's disease have been established and are currently in widespread use, for example, the administration of L-Dopa together with a decarboxylase inhibitor, such as L-carbidopa or benzerazide. The decarboxylase inhibitor protects the L-Dopa molecule from peripheral decarboxylation and thus ensures L-Dopa uptake by the remaining dopaminergic neurons in the striatum of the brain. Here the L-Dopa is converted into dopamine resulting in increased levels of dopamine in these neurons. In response to physiological impulses these neurons are therefore capable of releasing larger amounts of dopamine, the quantity of which approximates the normal required levels. This treatment therefore alleviates the symptoms of the disease and contributes to the well-being of the patients.

However, this L-Dopa treatment has its drawbacks, the main one being that its effectiveness is optimal only in the first few years following the onset of treatment. After this initial period the clinical response is diminished and is accompanied by adverse side effects which include dyskinesia, fluctuation in efficacy throughout the day ("on-off effect") and psychiatric symptoms such as confusional states, paranoia and hallucinations. This fall-off in the effect of L-Dopa treatment is attributed to a number of factors, including the natural progression of the disease, alteration in dopamine receptors as a consequence of increased dopamine production or increased levels of dopamine metabolites, and pharmacokinetic problems of L-Dopa absorption (reviewed by Youdim et al., Progress in Medicinal Chemistry, Vol. 21, Chapter 4, pp. 138–167 (1984), Eds. Ellis and West, Elsevier, Amsterdam).

In order to overcome the drawbacks of the L-Dopa treatment, various treatments have been devised in which L-Dopa is combined with MAO inhibitors, with the aim of reducing the metabolic breakdown of the newly formed dopamine (see for example, U.S. Pat. No. 4,826,875).

MAO exists in two forms known as MAO-A and MAO-B which have selectivity for different substrates and inhibitors. For example, MAO-B metabolizes more efficiently substrates such as 2-phenylethylamine and is selectively and irreversibly inhibited by (−)-deprenyl (as described below).

It should be noted, however, that combining L-Dopa with an inhibitor of both MAO-A and MAO-B is undesirable leading to adverse side effects related to an increased level of catecholamines throughout the neuraxis. Furthermore, complete inhibition of MAO is also undesirable as it potentiates the action of sympathomimetic amines such as tyramine leading to the so-called "cheese effect" (reviewed by Youdim et al., Handbook of Experimental Pharmacology, Vol. 90, Chap. 3 (1988) Eds, Trendelenburg and Weiner, Springer-Verlag). As MAO-B was shown to be the predominant form of MAO in the brain, selective inhibitors for this form were thus considered to be a possible way for achieving a decrease in dopamine breakdown on the one hand, together with a minimization of the systemic effects of total MAO inhibition, on the other.

One of these selective MAO-B inhibitors, (−)-deprenyl, has been extensively studied and has been used as an MAO-B inhibitor to augment L-Dopa treatment. This treatment with (−)-deprenyl is generally favorable, not causing the "cheese effect" at doses causing nearly complete inhibition of MAO-B (Elsworth et al., Physchopharmacology, 57, 33 (1978). Furthermore, addition of (−)-deprenyl to a combination of L-Dopa and decarboxylase inhibitor to Parkinson's patients leads to improvements in akinesia and overall functional capacity as well as the elimination of "on-off" type fluctuations (reviewed by Birkmayer & Riederer in "Parkinson's Disease" pp. 138–149, Springer-Verlag (1983)).

Thus, (−)-deprenyl enhances and prolongs the effect of L-Dopa and permits-a lowering of the dosage of L-Dopa whereby the adverse effects of L-Dopa treatment are limited.

However, (−)-deprenyl is not without its own adverse sides effects which include activation of pre-existing gastric ulcers and occasional hypertensive episodes. Furthermore, (−)-deprenyl is an amphetamine derivative and is metabolized to yield amphetamine and methamphetamines which may lead to undesirable side effects associated with these substances, e.g. increased heart rate (Simpson, Biochemical Pharmacology, 27, 1591 (1978); Finberg et al., in "Monoamine Oxidase Inhibitors—The State of the Art", pp. 31–43, Eds. Youdim and Paykel, (1981) Wiley).

Other compounds that are selective irreversible inhibitors of MAO-B but which are free of the undesirable effects associated with (−)-deprenyl have been described. One such compound, namely N-propargyl-1-aminoindan. HCl (racemic-PAI.HCl) was described in GB 1,003,686, GB 1,037,014 and U.S. Pat. No. 3,513,244. It is a potent, selective, irreversible inhibitor of MAO-B, is not metabolized to amphetamines and does not give rise to unwanted sympathomimetic effects.

In comparative animal tests racemic PAI was shown to have considerable advantages over (−)-deprenyl, for example, racemic PAI produced no significant tachycardia, did not increase blood pressure (effects produced by doses of 5 mg/kg of (−)-deprenyl), and did not lead to contraction of nictitating membrane nor to an increase in heart rate at doses up to 5 mg/kg (effects caused by (−)-deprenyl at doses over 0.5 mg/kg). Furthermore, racemic PAI.HCl does not potentiate the cardiovascular effects of tyramine (Finberg et al. in "Enzymes and Neurotransmitters in Mental Disease", pp. 205–219, (1980), Eds. Usdin et al., Pub. John Wiley and Sons, N.Y.; Finberg et al. (1981) in "Monoamine Oxidase Inhibitors—The State of the Art", ibid; Finberg and Youdim, British Journal Pharmacol. 85 451, (1985).

One object of this invention is to separate the racemic PAI compounds and to produce an enantiomer with MAO-B inhibition activity.

Since deprenyl has a similar structure to PAI and it is known that the (−)-enantiomer of deprenyl, i.e. (−)-deprenyl, is considerably more pharmaceutically active than the (+)-enantiomer, it was expected, by those skilled in the art, that only the (−) enantiomer of PAI would be the active MAO-B inhibitor.

However, contrary to such expectations, upon resolution of the enantiomers, it was found, in accordance with the present invention that the (+)-PAI enantiomer was in fact the active MAO-B inhibitor while the (−)enantiomer showed extremely low MAO-B inhibitory activity. Furthermore, the (+)PAI enantiomer surprisingly also had a higher degree of selectivity for MAO-B inhibition than the corresponding racemic form and may thus have less undesirable side effects in the treatment of the indicated disease. These findings are based on both in vitro and in vivo experiments as presented hereinafter in greater detail.

It was subsequently shown that (+)-PAI has the R absolute configuration. This was also surprising based on the expected structural analogy with deprenyl and the amphetamines.

The high degree of stereoselectivity of pharmacological activity between R(+)-PAI and the S(−) enantiomer is also remarkable. The compounds R(+)-PAI is nearly four orders of magnitude more active than the S(−) enantiomer in MAO-B inhibition. This ratio is significantly higher than that observed between the two deprenyl enantiomers (Knoll and Magyar, Adv. Biochem. Physchopharmacol., 5, 393 (1972); Magyar, et al., Acta Physiol. Acad. Sci. Hung., 32, 377 (1967). Furthermore, in some physiological tests, (+) deprenyl was reported to have equal or even higher activity than the (−) enantiomer (Tekes, et al., Pol. J. Pharmacol. Pharm. 40, 653 (1988).

N-methyl-N-propargylaminoindan (MPAI) is a more potent inhibitor of MAO activity, but with lower selectivity for MAO-B over A (Tipton, et al., Biochem. Pharmacol., 31, 1250 (1982)). Surprisingly, in this case we have found only small degree of difference in the relative activities of the two resolved enantiomers thus further emphasising the remarkableness of the case of R(+)-PAI. (See Table 1A).

Another object of the present invention is to provide for the first time use of the pharmaceutically active PAI-enantiomer alone (without L-Dopa) for treatment of Parkinson's disease, dementia and depression (see review by Youdim et al. in Handbook of Experimental Pharmacology, Vol. 90/I, (1988), chap.3, Eds. Trendelenberg and Wiener).

It is yet another object of the invention to provide for the use of the pharmaceutically active PAI-enantiomer for pretreatment alone or together with synergistic agents, of Parkinson's disease in order to delay the L-Dopa treatment and its associated adverse side effects. This approach has been studied with respect to (−)-deprenyl which was shown to be effective when administered alone to early Parkinsonism patients, and may also have a synergistic effect in these patients when administered together with α-tocopherol (a vitamin E derivative), (The Parkinson's Study Group, New England J. Med., 321(20), 1364–1371, (1989)).

In addition to its usefulness in treating Parkinson's disease, (−)-deprenyl has also been shown to be useful in the treatment of patients with dementia of the Alzheimer type (DAT) (Tariot et al., Psychopharmacology, 91, 489–495, 1987), and in the treatment of depression (Mendelewicz and Youdim, Brit. J. Psychiat. 142, 508–511, 1983). Thus, the R(+)-PAI compound of this invention has been shown to possess activity in restoration of memory, thus having potential for treatment of memory disorders, dementia and especially useful in Alzheimer's disease and for the treatment of the hyperactive syndrome in children.

DETAILED DESCRIPTION OF THE INVENTION

The present invention thus provides as a novel compound the R(+)-enantiomer of N-propargyl-1-aminoindan [R(+)PAI] of the formula (I):

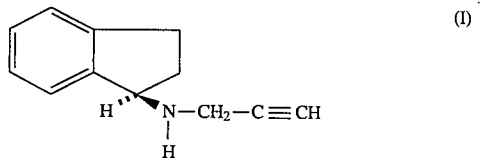

and pharmaceutically acceptable acid addition salts thereof. The present invention also relates to the preparation of R(+)PAI, to pharmaceutical compositions comprising the compound R(+)PAI together with suitable carriers and to the use of R(+)PAI for the treatment of human patients for Parkinson's disease, memory disorders, dementia of the Alzheimer type and hyperactive syndrome.

The R(+)PAI may be obtained by optical resolution of racemic mixtures of R and S-enantiomer of PAI. Such a resolution can be accomplished by any conventional resolution method, well known to a person skilled in the art, such as those described in "Enantiomers, Racemates and Resolutions" by J. Jacques, A. Collet and S. Wilen, Pub. John Wiley & Sons, N.Y., 1981. For example, the resolution may be carried out by preparative chromatography on a chiral column. Another example of a suitable resolution method is the formation of diastereomeric salts with a chiral acid such as tartaric, malic, mandelic acid or N-acetyl derivatives of aminoacids, such as N-acetyl leucine, followed by recrystallisation to isolate the diastereomeric salt of the desired R enantiomer.

The racemic mixture of R and S enantiomers of PAI may be prepared, e.g. as described in GB 1,003,676 and GB 1,037,014. The racemic mixture of PAI can also be prepared by reacting 1-chloroindan or 1-bromoindan with propargylamine. Alternatively, this racemate may be prepared by reacting propargylamine with 1-indanone to form the corresponding imine, followed by reduction of the carbon-nitrogen double bond of the imine with a suitable agent, such as sodium borohydride.

In accordance with this invention, the R enantiomer of PAI, can also be prepared directly from the optically active R-enantiomer of 1-aminoindan by reaction with propargyl bromide or propargyl chloride, in the presence of an organic or inorganic base and optionally in the presence of a suitable solvent.

Suitable organic or inorganic bases for use in the above reaction are, e.g., triethylamine, pyridine, alkali metal carbonates or bicarbonates etc. If the reaction is conducted in the presence of a solvent, this may be chosen from, e.g., toluene, methylene chloride and acetonitrile. A preferred method of preparation of the aforementioned compound is the reaction between R-1-aminoindan with propargyl chloride using potassium bicarbonate as a base and acetonitrile as solvent.

The above described reaction of 1-aminoindan generally results in a mixture of unreacted primary amine, the desired secondary amine and the tertiary amine N,N-bispropargylamino product. The desired secondary amine, i.e. N-propagyl-1-aminoindan, can be separated from this mixture by any conventional separation method, such as chromatography, distillation, selective extraction, etc.

The R-1-aminoindan starting material can be prepared by methods known from the literature, for example Lawson and Rao, Bichochemistry (1980) 19, 2133 and the references cited therein, and European Patent No. 235,590.

The R-1-aminoindan can also be prepared by resolution of a racemic mixture of the R and S enantiomers, e.g. by formation of diastereomeric salts with chiral acids, or by any other known method, such as those reported in the above mentioned "Enantiomers, Racemates and Resolutions" by J. Jacques et al, Pub. John Wiley & Sons, N.Y., 1981. Alternatively, the R-1-aminoindan starting material may be prepared by reacting 1-indanone with an optically active amine, followed by reduction of the carbon-nitrogen double bond of the resulting imine by hydrogenation over a suitable catalyst, such as palladium on carbon, platinum oxide, Raney-nickel etc. Suitable optically active amines are, for example, one of the antipodes of phenethylamine or an ester of an aminoacid, such as valine or phenylalanine. The benzylic N-C bond may be cleaved subsequently, by hydrogenation under non-vigorous conditions.

Additional methods for preparing R-1-aminoindan are the hydrogenation, as described above, of indan-1-one oxime ethers, wherein the alkyl portion of the ether contains an optically pure chiral center. Alternatively, a non-chiral derivative of indan-1-one containing a carbon-nitrogen double bond, such as an imine or oxime, can be reduced with a chiral reducing agent, e.g. a complex of lithium aluminium-hydride and ephedrine.

For the preparation of pharmaceutically acceptable acid addition salts of the compound of R(+)PAI, the free base can be reacted with the desired acids in the presence of a suitable solvent by conventional methods. Similarily, an acid addition salt may be converted to the free base form in a known manner.

In accordance with the present invention, the compound R(+)PAI may be prepared as pharmaceutical compositions particularly useful for the treatment of Parkinson's disease, dementia of the Alzheimer type (DAT) or depression. Such compositions may comprise the compound of R(+)PAI or pharmaceutically acceptable acid addition salts thereof, together with pharmaceutically acceptable carriers and/or excipients. For example, these compositions may be prepared as medicaments to be administered orally, parenterally, rectally or transdermally. Suitable forms for oral administration include tablets, compressed or coated pills, dragees, sachets, hard or soft gelatin capsules, sub-lingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

These above compositions may be used alone to treat Parkinson's disease, Alzheimer's disease or depression, or alternatively, in the case of Parkinson's disease, they may be used as an adjunct to the conventional L-Dopa treatments. A pharmaceutical composition for oral use in the form of tablets or capsules may comprise R(+)-N-propargyl-1-aminoindan, Levodopa, and a decarboxylase inhibitor. A composition may comprise 2–20 mg of R(+)-N-propargyl-1-aminoindan, 50–250 mg of Levodopa, and 10–25 mg of L-Carbidopa. A composition may comprise 2–10 mg of R(+)-N-propargyl-1-aminoindan, 50–200 mg of Levodopa, and 12.5–50 mg of benserazide.

The preferred dosages of the active ingredient, i.e., R-PAI compounds, in the above compositions are within the following ranges: for oral or suppository formulations 2–20 mg per dosage unit to be taken daily and more preferably 5–10 mg per dosage unit to be taken daily may be used; and for injectable formulations 1–10 mg/ml per dosage unit to be taken daily and more preferably 2–5 mg/ml per dosage unit to be taken daily may be used.

Figure 1:
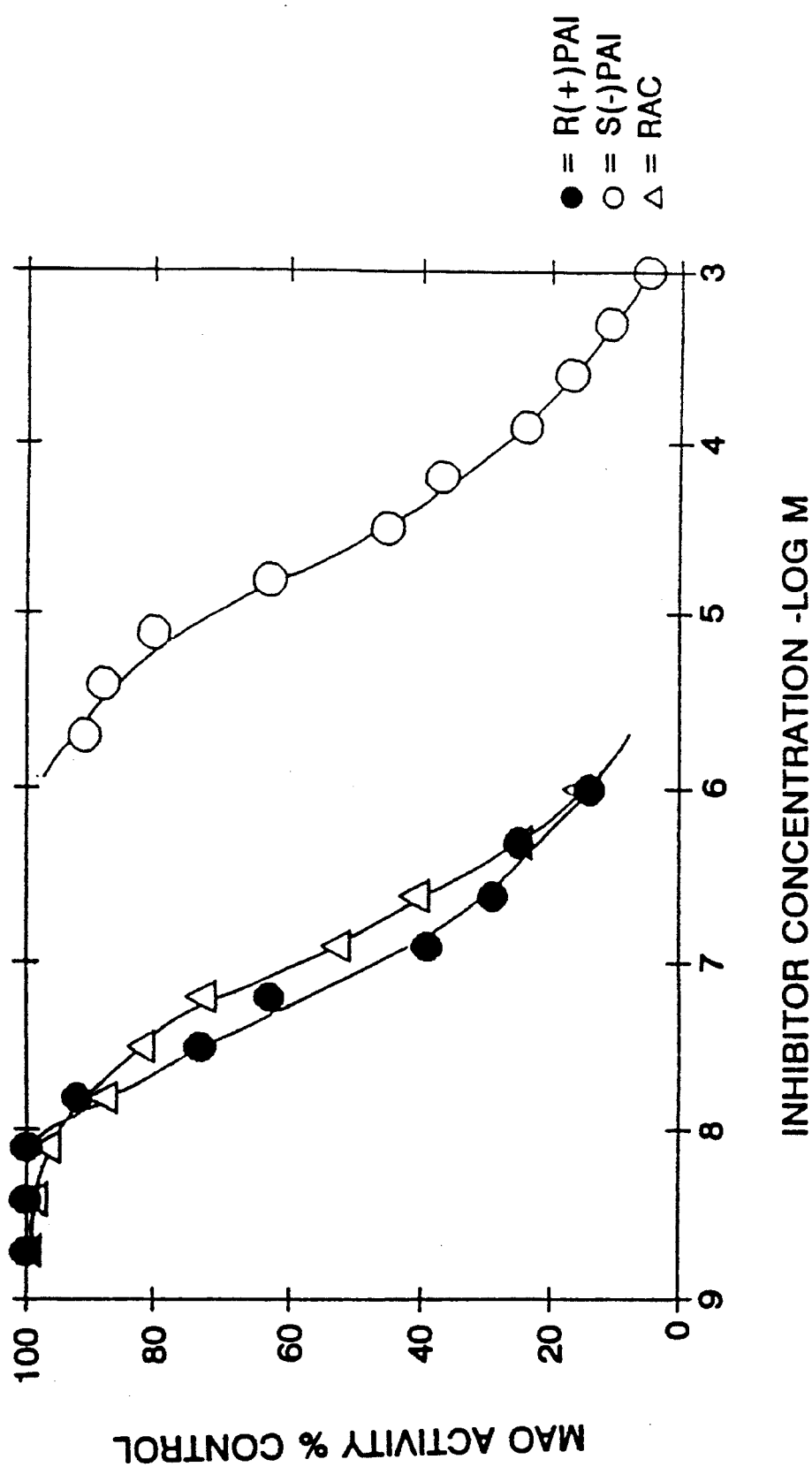
FIG. 1 is a graphic representation of the results according to Example 19.

The invention will now be described in more detail in the following non-limiting examples and their accompanying Tables and Figures.

EXAMPLE 1

Racemic N-propargyl-1-aminoindan hydrochloride

Racemic 1-aminoindan (10.0 g) and 10.4 g of potassium carbonate were added to 75 ml of acetonitrile. The resulting suspension was heated to 60° C. and 4.5 g of propargyl chloride were added dropwise.

The mixture was stirred at 60° C. for 16 hours, whereafter most of the volatiles were removed by distillation in vacuo. The residue was partitioned between 10% aqueous sodium hydroxide and methylene chloride.

The organic phase was dried and the solvent removed by distillation. The residue was flash chromatographed on silica gel, eluting with 40% ethyl acetate/60% hexane. The fractions containing the title compound as a free base were combined and the eluant replaced by ether. The ethereal solution was treated with gaseous HCl, the precipitate formed was isolated by suction filtration and recrystallized from isopropanol to yield 7.3 g of the title compound, m.p. 182°–4° C.

Chromatographic and spectroscopic data were in accordance with the literature (U.S. Pat. No. 3,513,244) and an authentic sample.

NMR (δ, $CDCl_3$): 2.45 (2H, m), 2.60 (1H, t), 2.90 (1H, m), 3.45 (1H, m), 3.70 (2H, d), 4.95 (1H, t), 7.5 (4H, m) ppm.

EXAMPLE 2

S-(−)-N-Propargyl-1-aminoindan hydrochloride

The title compound in free base form was isolated by resolving the racemic mixture of the free base of Example 1 on a Chiracel OJ (cellulose tris[p-methylbenzoate]) preparative HPLC column eluting with 10% isopropanol/90% hexane and collecting the first eluted major peak. The resulting oil was converted to the title compound (hydrochloride) by treatment of a 10% diethyl ether solution of the oil with gaseous HCl and the resulting precipitate was collected by suction filtration.

$[\alpha]_D$–29.2° (1%, ethanol), m.p. 182°–184° C. Other chromatographic and spectroscopic properties were identical with the hydrochloride salt of Example 1.

EXAMPLE 3

R-(+)-N-Propargyl-1-aminoindan hydrochloride

The title compound was prepared as in Example 2 above, except that the second eluted peak from the preparative HPLC was collected; $[\alpha]_D$+29.1° (0.8%, ethanol), m.p. 179°–181° C. Other chromatographic and spectroscopic properties were identical with the hydrochloride salt of Example 1.

EXAMPLE 4

R-(+)-N-propargyl-1-aminoindan hydrochloride

R-(−)-1-aminoindan (12.4 g) and 12.9 g of potassium carbonate were added to 95 ml of acetonitrile. The resulting suspension was heated to 60° and 5.6 g of propargyl chloride were added dropwise. The mixture was stirred at 60° C. for 16 hours, whereafter most of the volatiles were removed by distillation in vacuo. The residue was partitioned between 10% aqueous sodium hydroxide and methylene chloride.

The organic phase was dried and the solvent removed in vacuo, the residue was flash chromatographed on silica gel eluting with 40% ethyl acetate/60% hexane. Fractions containing the free base of the title compound were combined and the solvent replaced by ether. The ethereal solution was treated with gaseous HCl and the resulting precipitate was isolated by suction filtration and recrystallized from isopropanol to yield 6.8 g of the title compound, m.p. 183°–185° C., $[\alpha]_D$+30.90 (2%, ethanol). Spectral properties were identical to those reported for the compound of Example 1.

EXAMPLE 5

S-(−)-N-propargyl-1-aminoindan hydrochloride

The title compound was prepared by the method of Example 4, except that S-(+)-1-aminoindan was used as starting material. The product exhibited $[\alpha]_D$–30.3 (2%, ethanol ), m.p. 183°–5° C. Spectral properties were identical to those reported for the compound of Example 1.

EXAMPLE 6

Di (R-(+)-N-propargyl-1-aminoindan)L-tartarate

To a solution of L-Tartaric acid (4.4 g ) in 48 ml of boiling methanol was added a solution of R-(+)-N-propargyl-1-aminoindan free base (5.0 g) in methanol (48 ml ). The solution was heated to reflux and 284 ml of t-butylmethyl ether was added over 20 minutes. The mixture was heated for an additional 30 minutes, cooled, and the resulting precipitate was isolated by suction filtration to yield 6.7 g of the title compound, m.p. 175°–177° C. $[\alpha]_D$ (1.5, $H_2O$)=+34.3; Anal. calcd. for $C_{28}H_{32}O_6N_2$; C, 68.26, H, 6.56, N, 5.69. Found: C., 68.76; H, 6.57; N, 5.61.

EXAMPLE 7

R-(+)-N-Methyl-N-propargyl-1-aminoindan hydrochloride

The free base form of R-(+)-N-propargyl-1-aminoindan from Example 4 (1.2 grams), potassium carbonate (0.97 grams) and methyl iodide (1 gram) were added to 15 ml of acetone and the resulting suspension heated to reflux under a nitrogen atmosphere for 8 hrs. Thereafter the volatiles were removed under reduced pressure and the residue partitioned between 10% aqueous sodium hydroxide (30 ml) and methylene chloride (30 ml). The organic phase was dried and the solvent removed in vacuo. The residue was flash chromatographed on silica gel eluting with 40% ethyl acetate/60% hexane. Fractions containing the title compound as a free base were combined and the solvent replaced by diethyl ether. The ethereal solution was treated with gaseous HCl, the volatiles removed in vacuo and the residue recrystallized from isopropanol to yield 400 mg of the title compound as a white crystalline solid, m.p.: 134°–136° C. $[\alpha]_D$+31.40 (ethanol). NMR(δ$CDCl_3$):2.55 (2H, m); 2.7 (1H, br.s); 2.8 (3H, s); 3.0 (1H, m); 3.4 (1H, m); 3.9 (2H, br.s): 5.05 (1H, m) 7.7 (4H, m) ppm.

EXAMPLE 8

S-(−)-N-methyl-propargyl-1-aminoindan hydrochloride

The title compound was prepared as in Example 7 above, except that S-(−)-N-propargyl-1-aminoindan (free base) from Example 5 was used as starting material. All of the physical and spectral properties of the title compound were identical to those in Example 7 except for the $[\alpha]_D$–34.9° (ethanol).

EXAMPLE 9

| Tablet Composition | |
| --- | --- |
| R(+)-N-propargyl-1-aminoindan hydrochloride | 5.0 mg |
| Pregelatinized starch | 47.0 mg |
| Lactose hydrous | 66.0 mg |
| Microcrystalline cellulose | 20.0 mg |
| Sodium starch glycolate | 3.0 mg |
| Talc | 1.5 mg |
| Magnesium stearate | 0.7 mg |

Purified water added as required for granulation.

EXAMPLE 10

| Tablet Composition | |
| --- | --- |
| R(+)-N-propargyl-1-aminoindan hydrochloride | 1.0 mg |
| Lactose hydrous | 50.0 mg |
| Pregelatinized starch | 36.0 mg |
| Microcrystalline cellulose | 14.0 mg |
| Sodium starch glycolate | 2.2 mg |
| Talc | 1.0 mg |
| Magnesium stearate | 0.5 mg |

Purified water added as required for granulation.

EXAMPLE 11

| Capsule Composition | |
| --- | --- |
| R(+)-N-propargyl-1-aminoindan hydrochloride | 5.0 mg |
| Pregelatinized starch | 10.0 mg |
| Starch | 44.0 mg |
| Microcrystalline cellulose | 25.0 mg |
| Ethylcellulose | 1.0 mg |
| Talc | 1.5 mg |

Purified water added as required for granulation.

EXAMPLE 12

| Injection Composition | |
| --- | --- |
| R(+)-N-propargyl-1-aminoindan hydrochloride | 5.0 mg |
| Dextrose anhydrous | 44.0 mg |

HCl added to pH 5

Purified water added as required for 1 ml

EXAMPLE 13

| Injection Composition | |
| --- | --- |
| R(+)-N-propargyl-1-aminoindan hydrochloride | 1.0 mg |
| Sodium chloride | 8.9 mg |

HCl added to pH 5

Purified water added as required to 1 ml

EXAMPLE 14

| Injection Composition | |
| --- | --- |
| R(+)-N-propargyl-1-aminoindan hydrochloride | 2.0 mg |
| Sodium chloride | 8.9 mg |

HCl added to pH 5

Purified water added as required to 1 ml

EXAMPLE 15

| Syrup Composition | |
| --- | --- |
| R(+)-N-propargyl-1-aminoindan hydrochloride | 5.0 mg |
| Sucrose | 2250.0 mg |
| Saccharin sodium | 5.0 mg |
| Methylparaben | 6.0 mg |
| Propylparaben | 1.0 mg |
| Flavor | 20.0 mg |
| Glycerin USP | 500 mg |
| Alcohol 95% USP | 200 mg |

Purified water as required to 5.0 ml

EXAMPLE 16

| Sublingual Tablets | |
| --- | --- |
| R(+)-N-propargyl-1-aminoindan hydrochloride | 2.5 mg |
| Microcrystalline cellulose | 20.0 mg |
| Lactose hydrous | 5.0 mg |
| Pregelatinized starch | 3.0 mg |
| Povidone | 0.3 mg |
| Coloring agent | q.s. |
| Flavor | q.s. |
| Sweetener | q.s. |
| Talc | 0.3 mg |

Blend the excipients and the active and granulate with an ethanol solution of Povidone. After drying and weighing, it is blended with the talc and compressed.

EXAMPLE 17

| PAI Sublingual Tablets | |
| --- | --- |
| R(+)-N-propargyl-1-aminoindan hydrochloride | 5.0 mg |
| Microcrystalline cellulose | 15.0 mg |
| Pregelatinized starch | 12.0 mg |
| Ethyl cellulose | 0.3 mg |
| Talc | 0.3 mg |

Purified water added as required for granulation.

EXAMPLE 18

| Tablet Composition | |
| --- | --- |
| R(+)-N-propargyl-1-aminoindan hydrochloride | 5.0 mg |
| Levodopa | 100.0 mg |
| Carbidopa | 25.0 mg |
| Pregelatinized starch | 24.0 mg |
| Starch | 40.0 mg |
| Microcrystalline cellulose | 49.5 mg |
| Col. D & C Yellow No. 10 | 0.5 mg |
| Col. D & C Yellow No. 6 | 0.02 mg |

Alcohol USP added as required for granulation.

The following Examples and their accompanying Tables and Figures relate to the Biological Experiments carried out in accordance with this invention.

EXAMPLE 19

Inhibition of MAO activity in vitro
Experimental protocol

The MAO enzyme source was a homogenate of rat brain in 0.3M sucrose, which was centrifuged at 600 g for 15 min. The supernatant was diluted appropriately in 0.05M phosphate buffer, and pre-incubated with serial dilutions of compounds of general formula I: R(+)-PAI, S(−)-PAI and racemic-PAI (wherein A is hydrogen) for 20 min at 37° C. $^{14}$C-labelled substrates (2-phenylethylamine, hereinafter PEA; 5-hydroxytryptamine, hereinafter 5-HT) were then added, and the incubation continued for a further 20 min (PEA), or 30–45 min (5-HT). Substrate concentrations used were 50 uM (PEA), and 1 mM (5-HT). In the case of PEA, enzyme concentration was chosen so that not more than 10% of the substrate was metabolized during the course of the reaction. The reaction was then stopped by addition of tranylcypromine (to final concentration 1 mM), and the incubate filtered over a small column of Amberlite CG-50, buffered to pH 6.3. The column was washed with 1.5 ml water, the eluates pooled and the radioactive content determined by liquid scintillation spectrometry. Since the amine substrates are totally retained on the column, radioactivity in the eluate indicates the production of neutral and acidic metabolites formed as a result of MAO activity. Activity of MAO in the sample was expressed as a percentage of control activity in the absence of inhibitors, after subtraction of appropriate blank values. The activity determined using PEA as substrate is referred to as MAO-B, and that determined using 5-HT as MAO-A.

Figure 2:
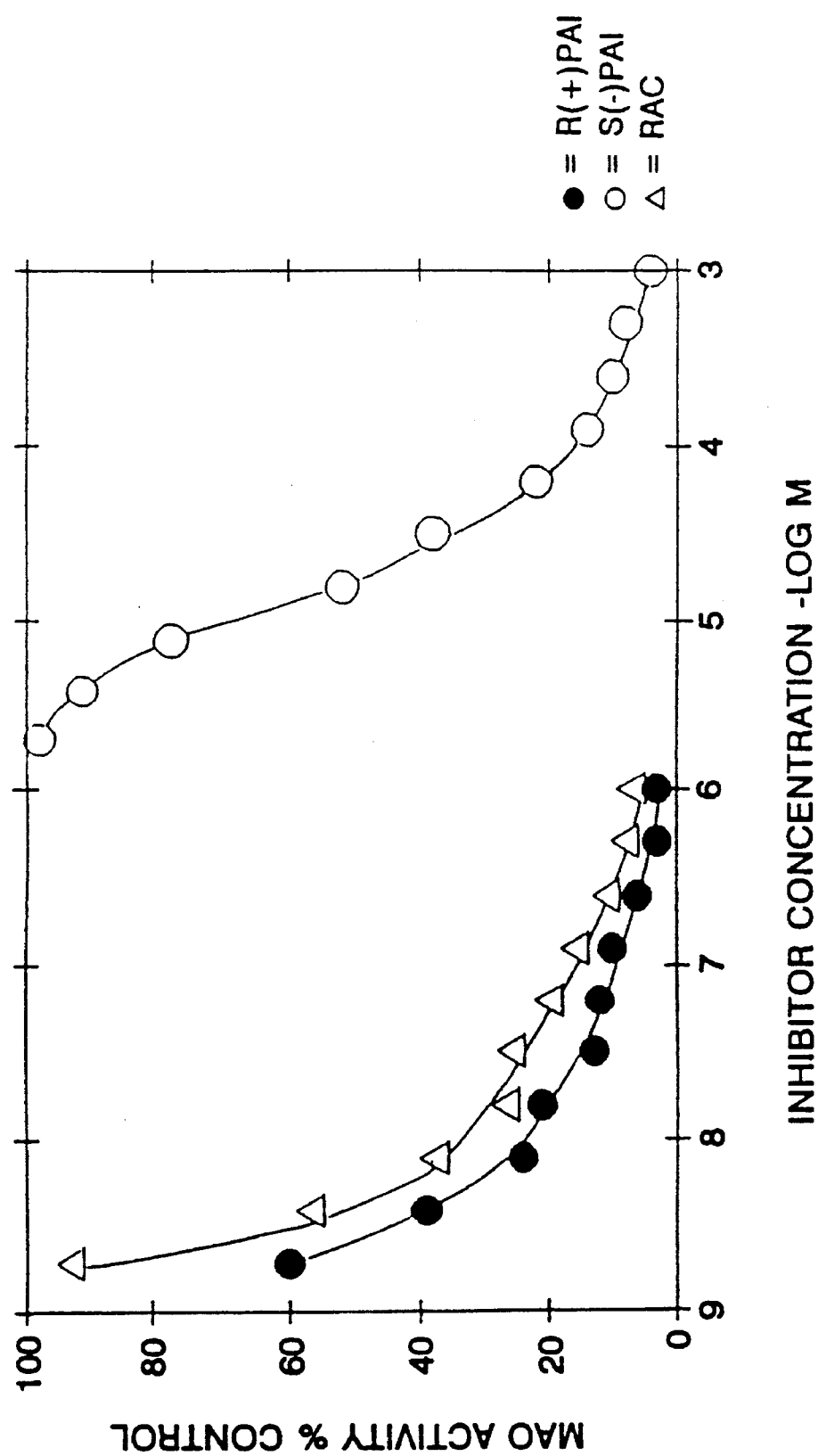
FIG. 2 is a graphic representation of the results according to Example 19.

Results:

Inhibitory activity of the R(+)-PAI, S(−)-PAI and racemic-PAI compounds of formula I were examined separately in vitro, and the results of typical experimental runs are shown in FIGS. 1 and 2. The entire experiment was repeated three times. Concentration of inhibitor producing 50% inhibition of substrate metabolism (IC-50) was calculated from the inhibition curves, and is shown in Table 1. From this data it can be seen that:

(a) the R(+)-PAI is twice as active as the racemate for inhibition of MAO-B;

(b) the R(+)-PAI is 29 times more active for inhibition of MAO-B than MAO-A;

(c) the S(−)-PAI is only 1/6,800 as active as the R(+)-PAI for inhibition of MAO-B, and shows little or no selectivity between MAO-B and MAO-A.

TABLE 1

IC-50 (nM) VALUES FOR INHIBITION OF MAO-A AND MAO-B BY RACEMIC-PAI AND THE R(+) AND S(−) ENANTIOMERS THEREOF IN RAT BRAIN HOMOGENATE IN VITRO

| | IC-50 (nM) | | | | | |
|---|---|---|---|---|---|---|
| | MAO-A | | | MAO-B | | |
| Compound: | S(−)PAI | R(+)PAI | Rac | S(−)PAI | R(+)PAI | Rac |
| | 26000 | 73 | 140 | 17000 | 2.5 | 5 |

The results of the same experiment using R(+) and S(−) MPAI (N-methyl-N-propargyl-1-aminoindan) are reported in Table 1A. Each of the enantiomers of MPAI is less selective between MAO-B and MAO-A inhibition than R(+)PAI. Furthermore, R(+)MPAI is only five times as active as S(−)MPAI in MAO-B inhibition, in contrast to R(+)PAI which is about 7000 times as active as S(−)PAI in this assay.

TABLE 1A

IC-50 (nM) VALUES FOR INHIBITION OF MAO-A AND MAO-B BY THE R(+) AND S(−) ENANTIOMERS OF MPAI IN RAT BRAIN HOMOGENATE IN VITRO

| | IC-50 (nM) | | | |
|---|---|---|---|---|
| | MAO-A | | MAO-B | |
| Compound: | S(−)MPAI | R(+)MPAI | S(−)MPAI | R(+)MPAI |
| | 70 | 3 | 50 | 10 |

Figure 3A:
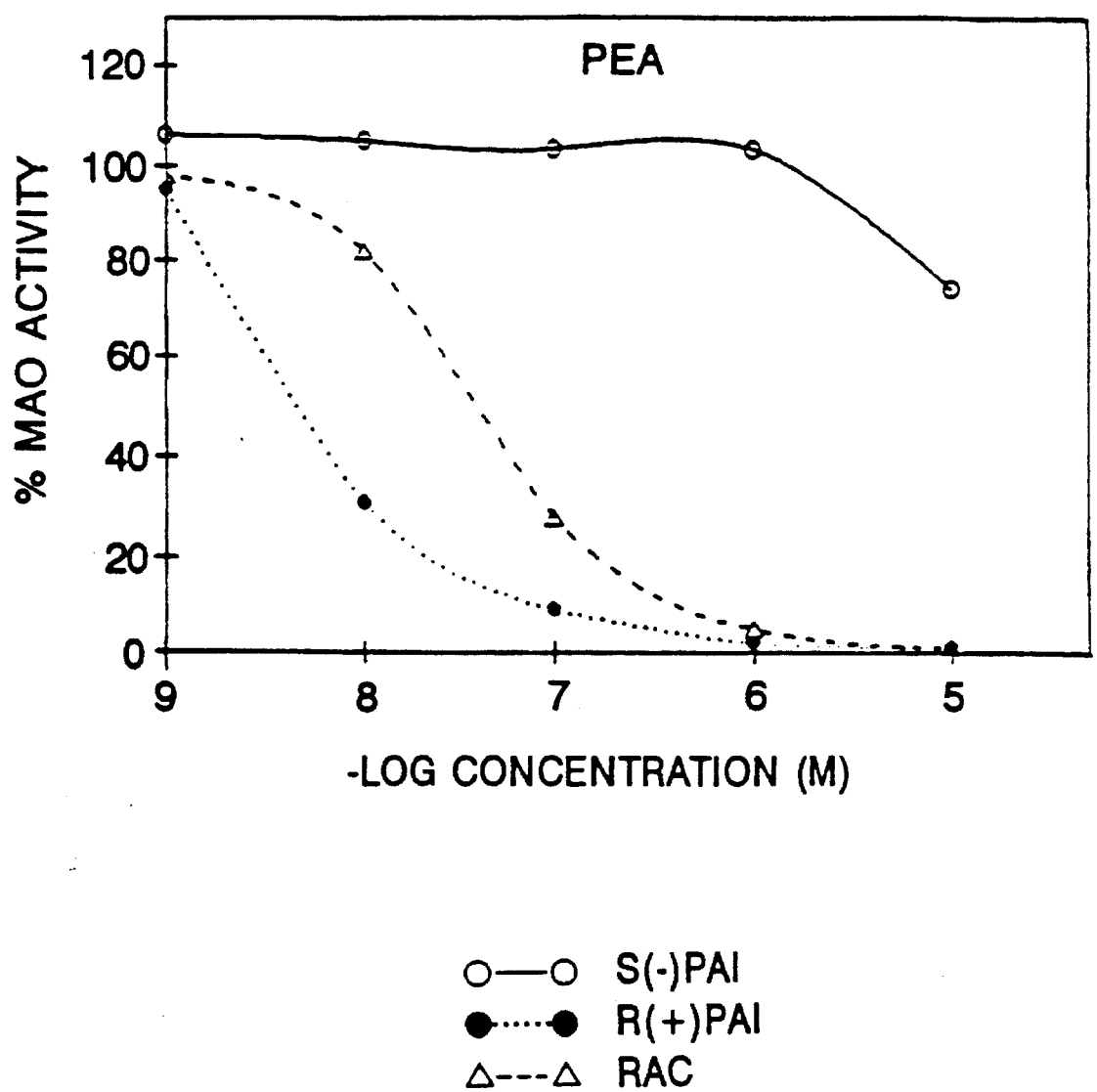
FIG. 3A is a graphic representation of the results according to Example 19.
Figure 3B:
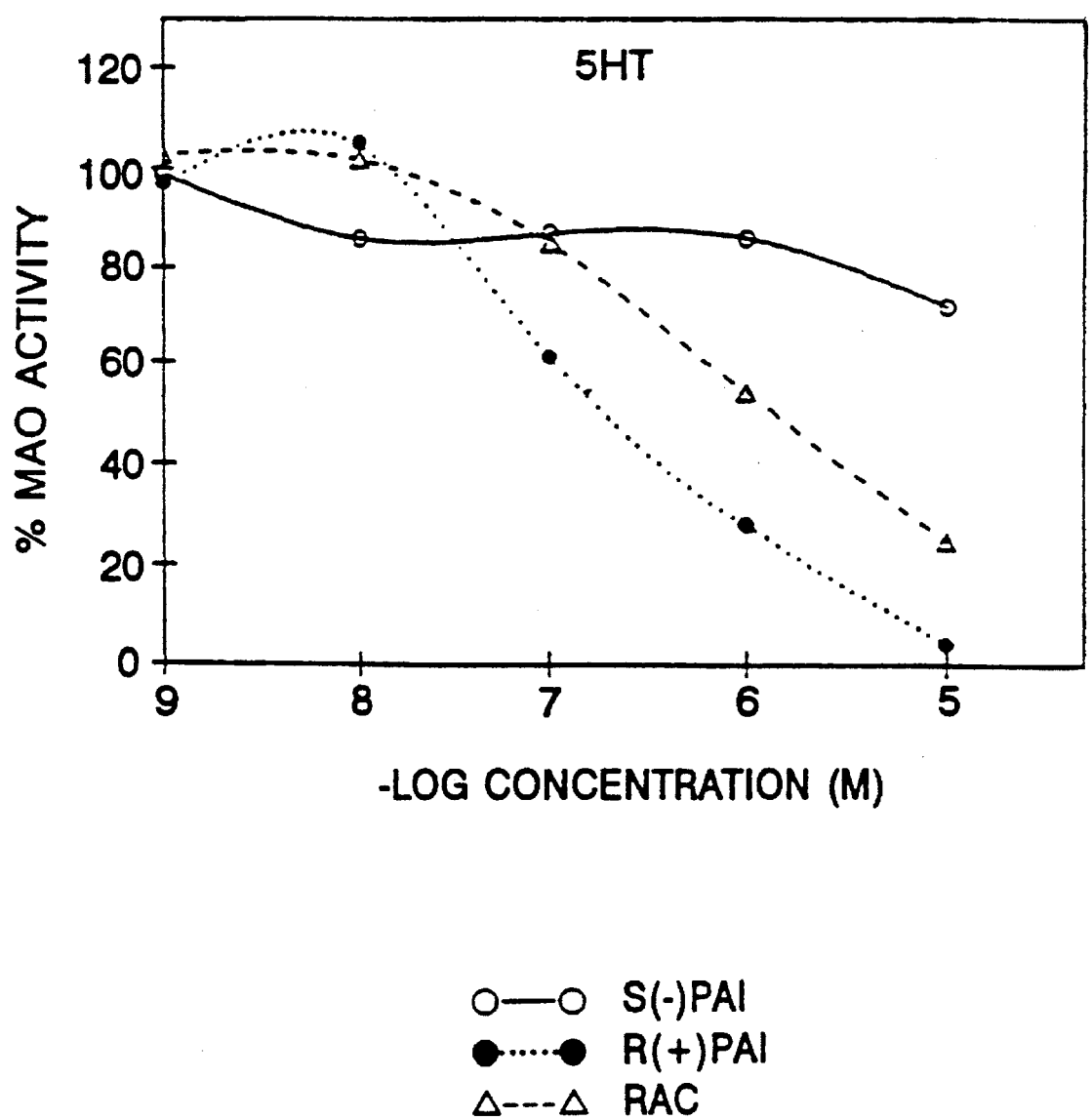
FIG. 3B: see description of FIG. 3A
Figure 4:
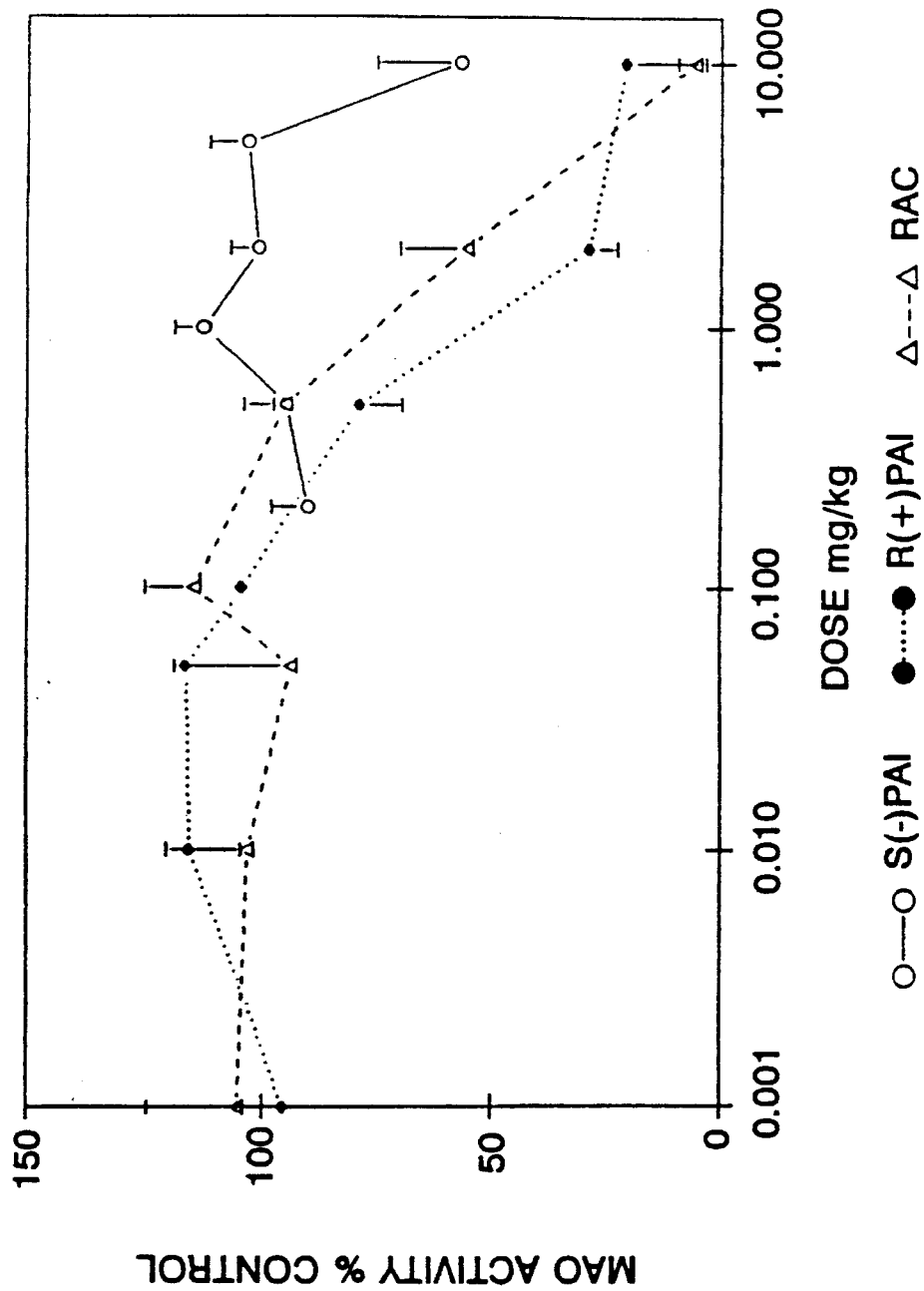
FIG. 4 is a graphic representation of the results according to Example 20.
Figure 5:
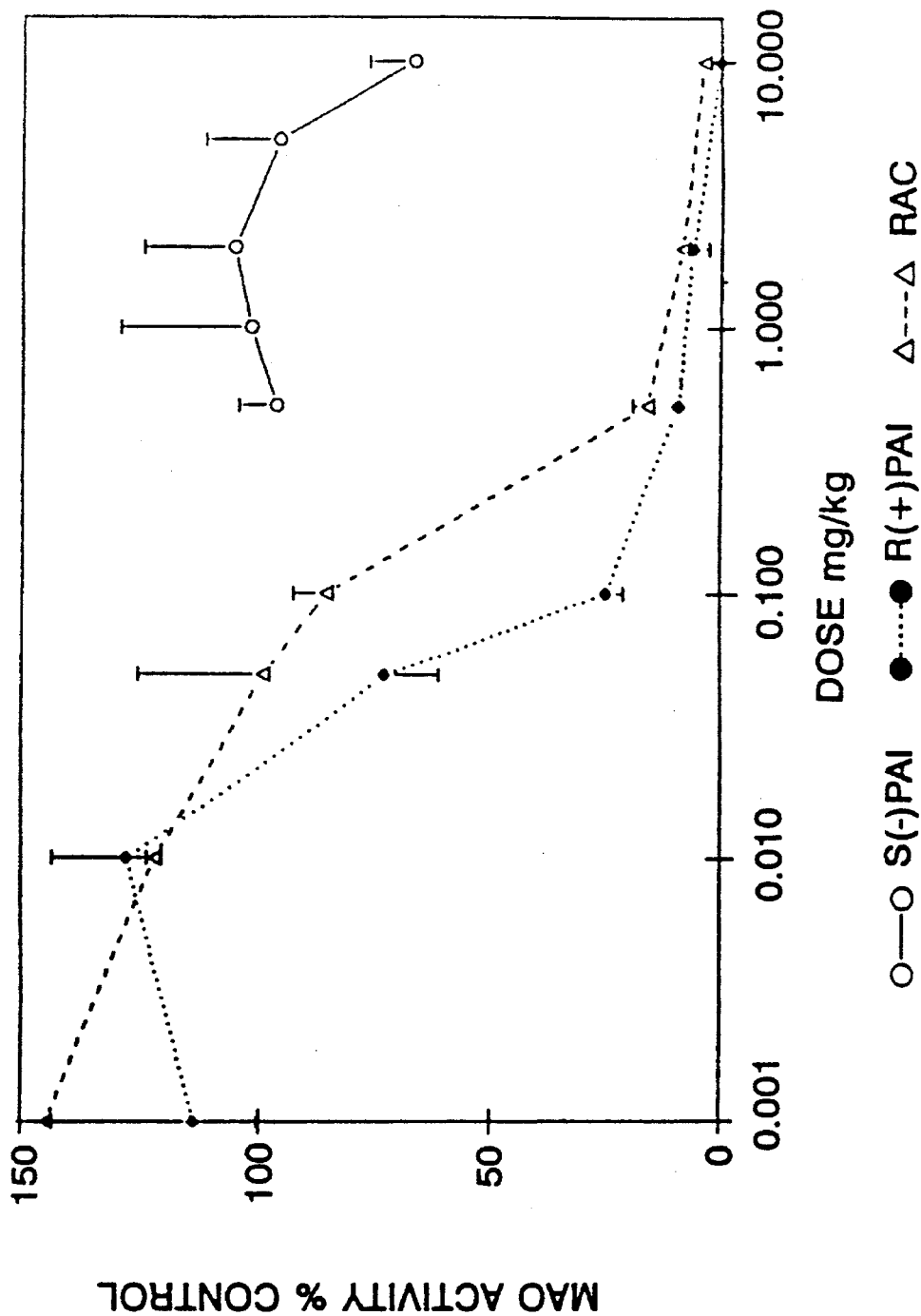
FIG. 5 is a graphic representation of the results according to Example 20.
Figure 6:
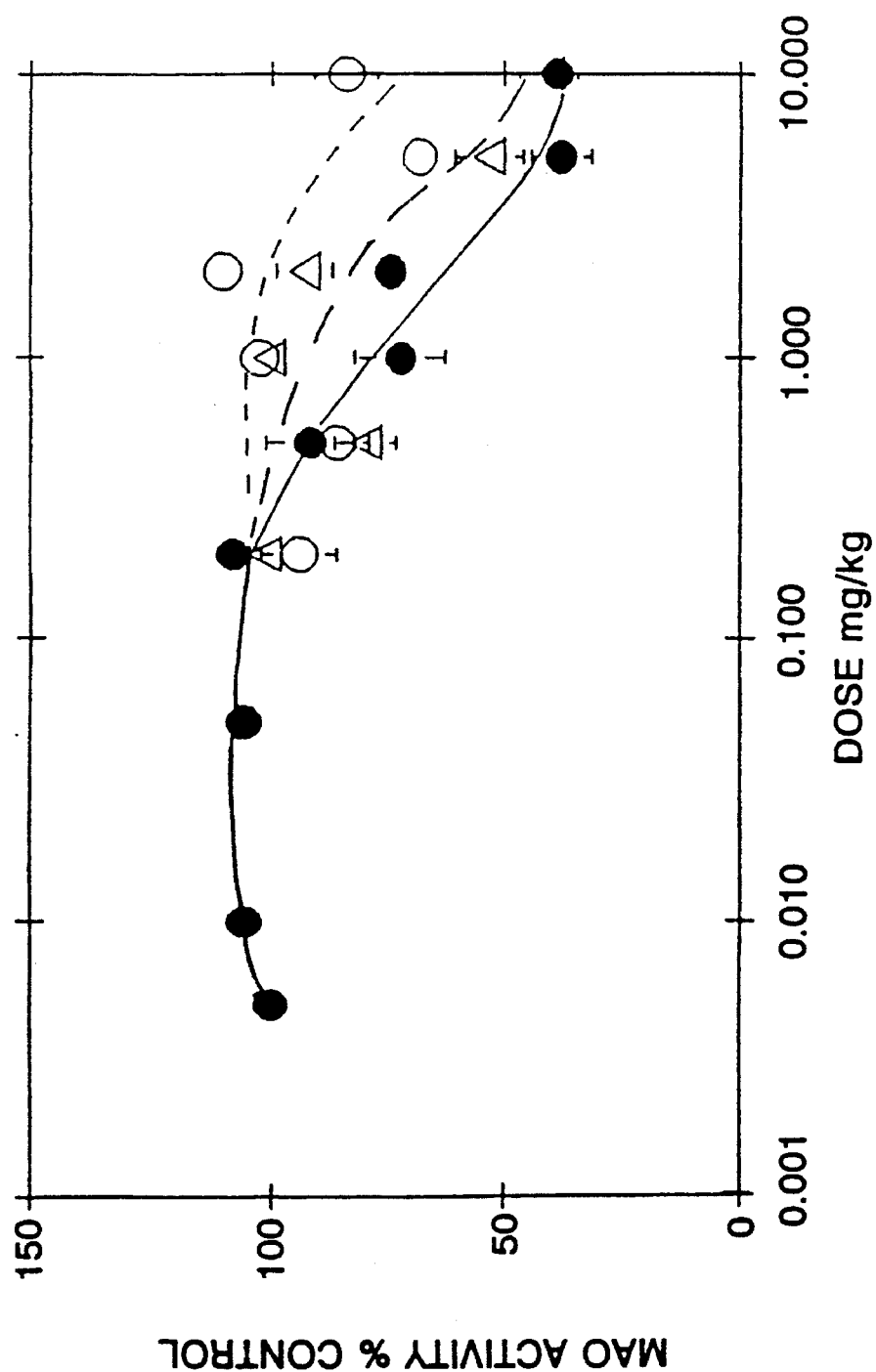
FIG. 6 is a graphic representation of the results according to Example 20.
Figure 7:
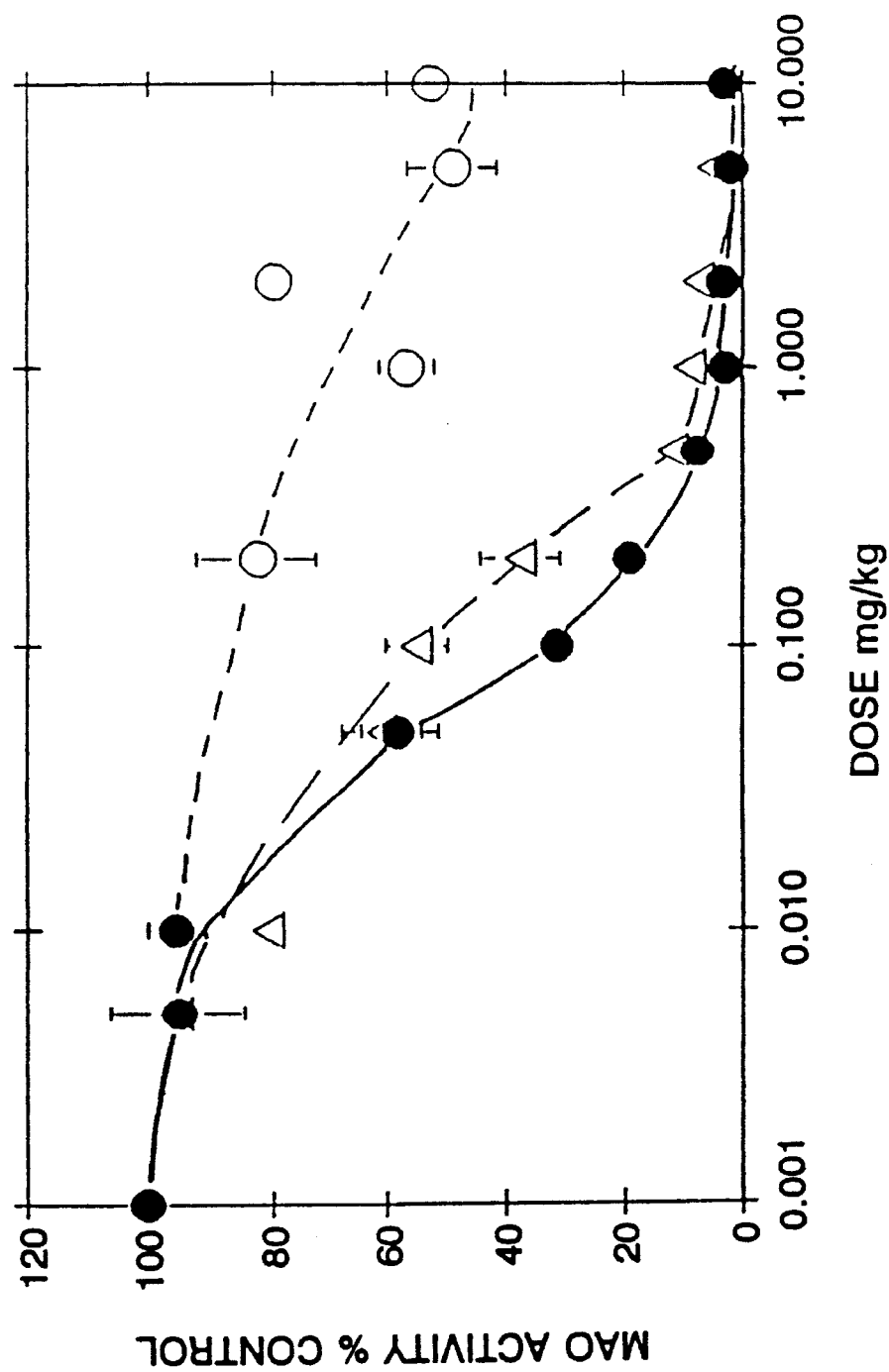
FIG. 7 is a graphic representation of the results according to Example 20.
Figure 8:
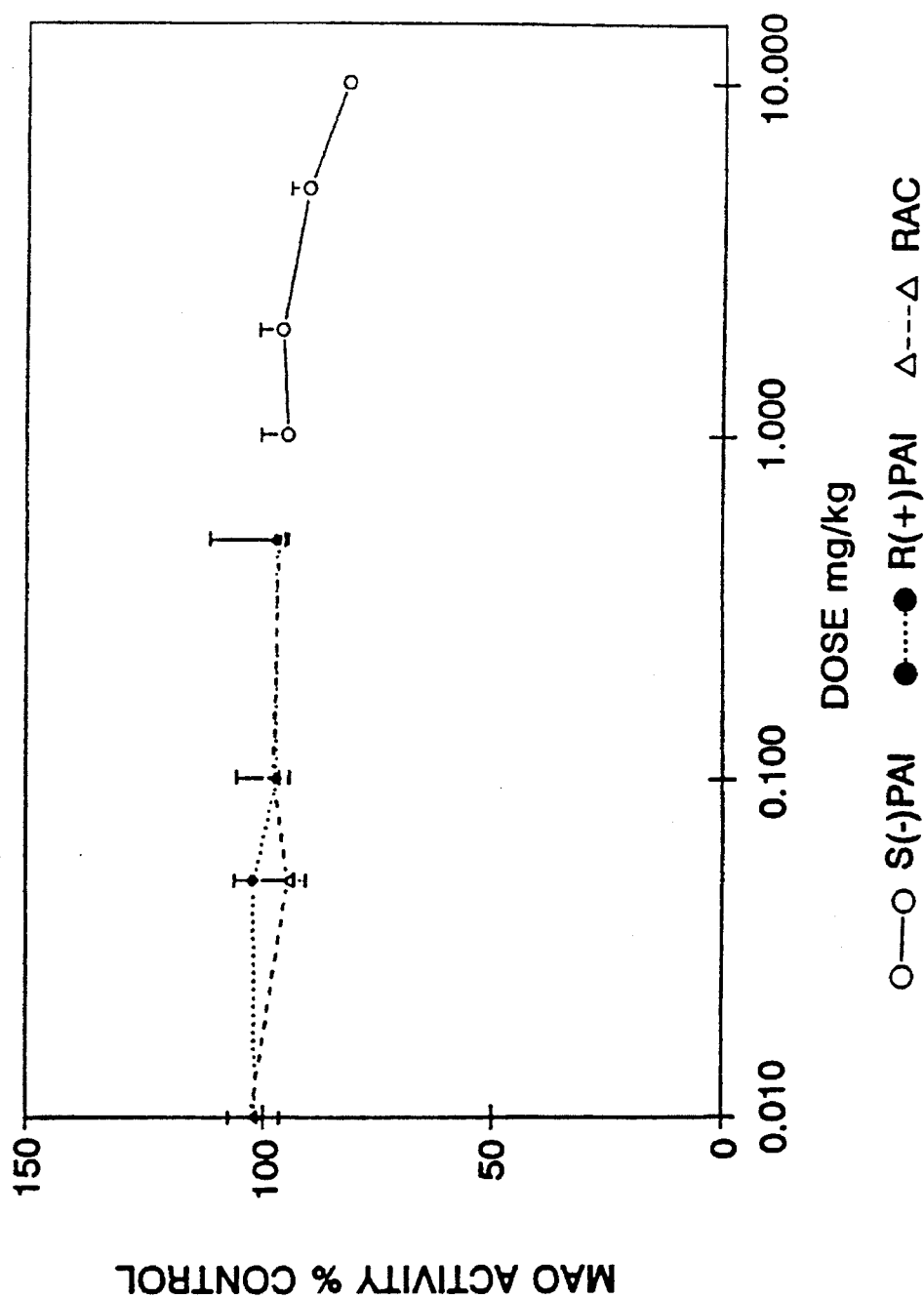
FIG. 8 is a graphic representation of the results according to Example 20.
Figure 9:
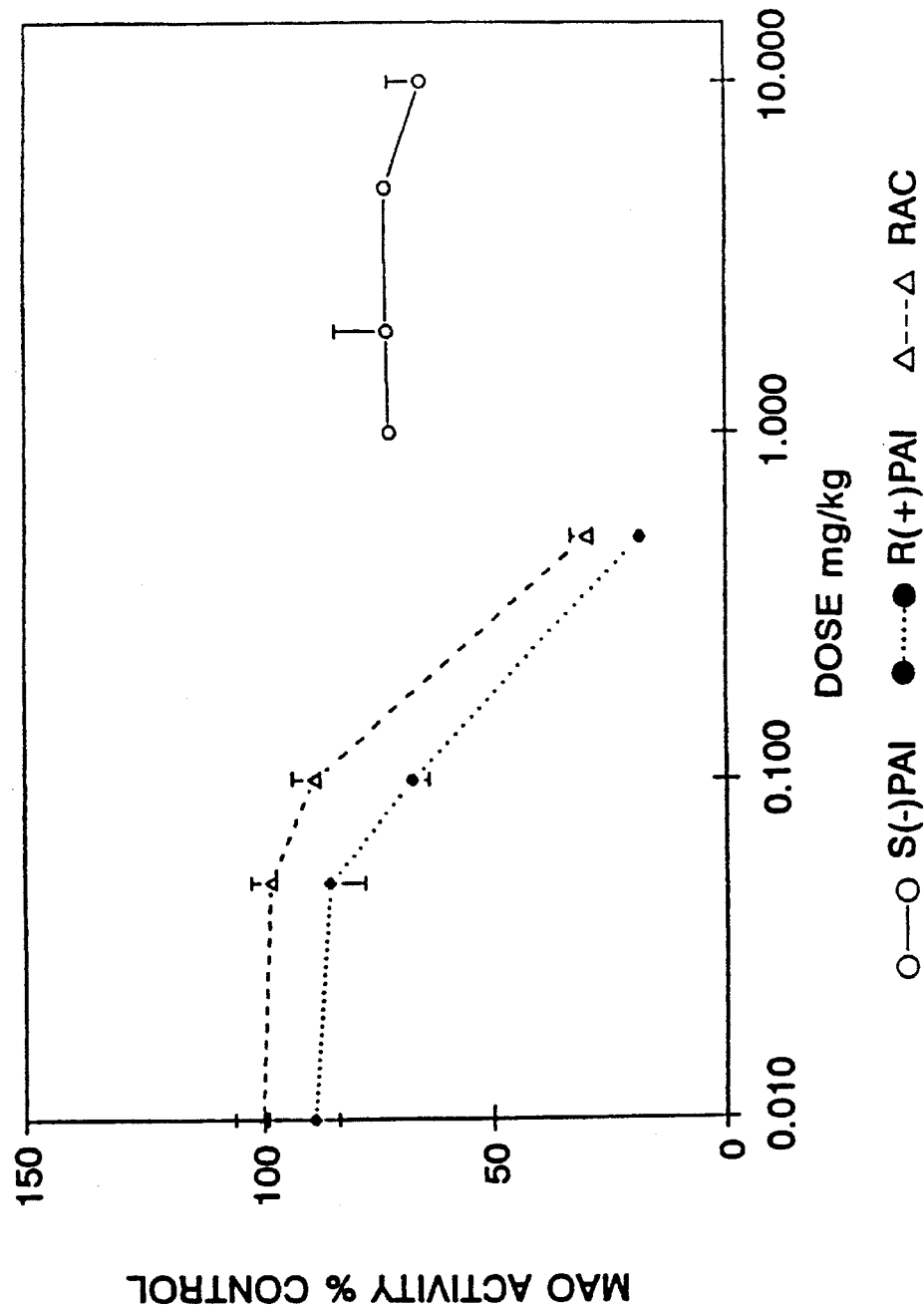
FIG. 9 is a graphic representation of the results according to Example 20.
Figure 10:
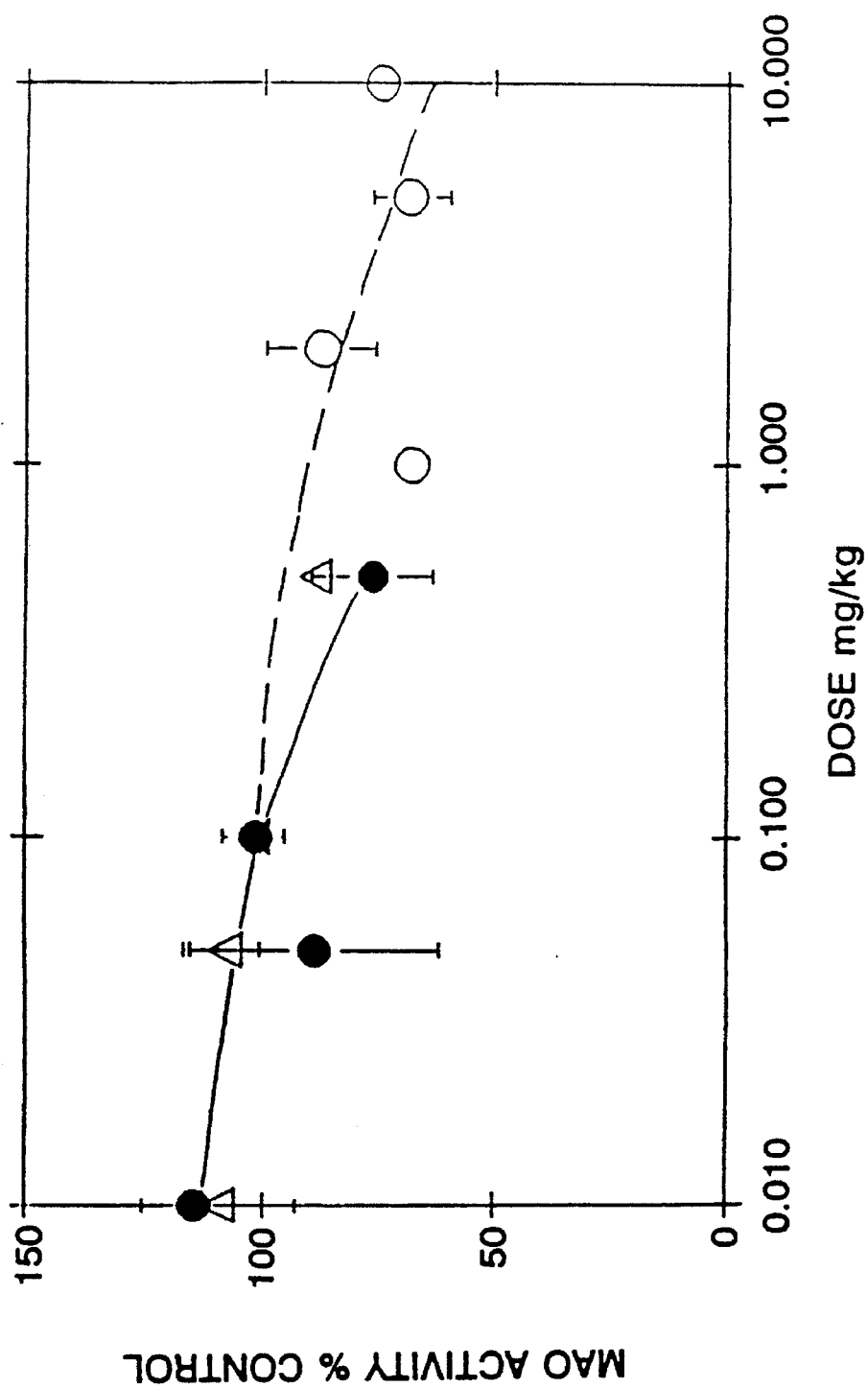
FIG. 10 is a graphic representation of the results according to Example 20.
Figure 11:
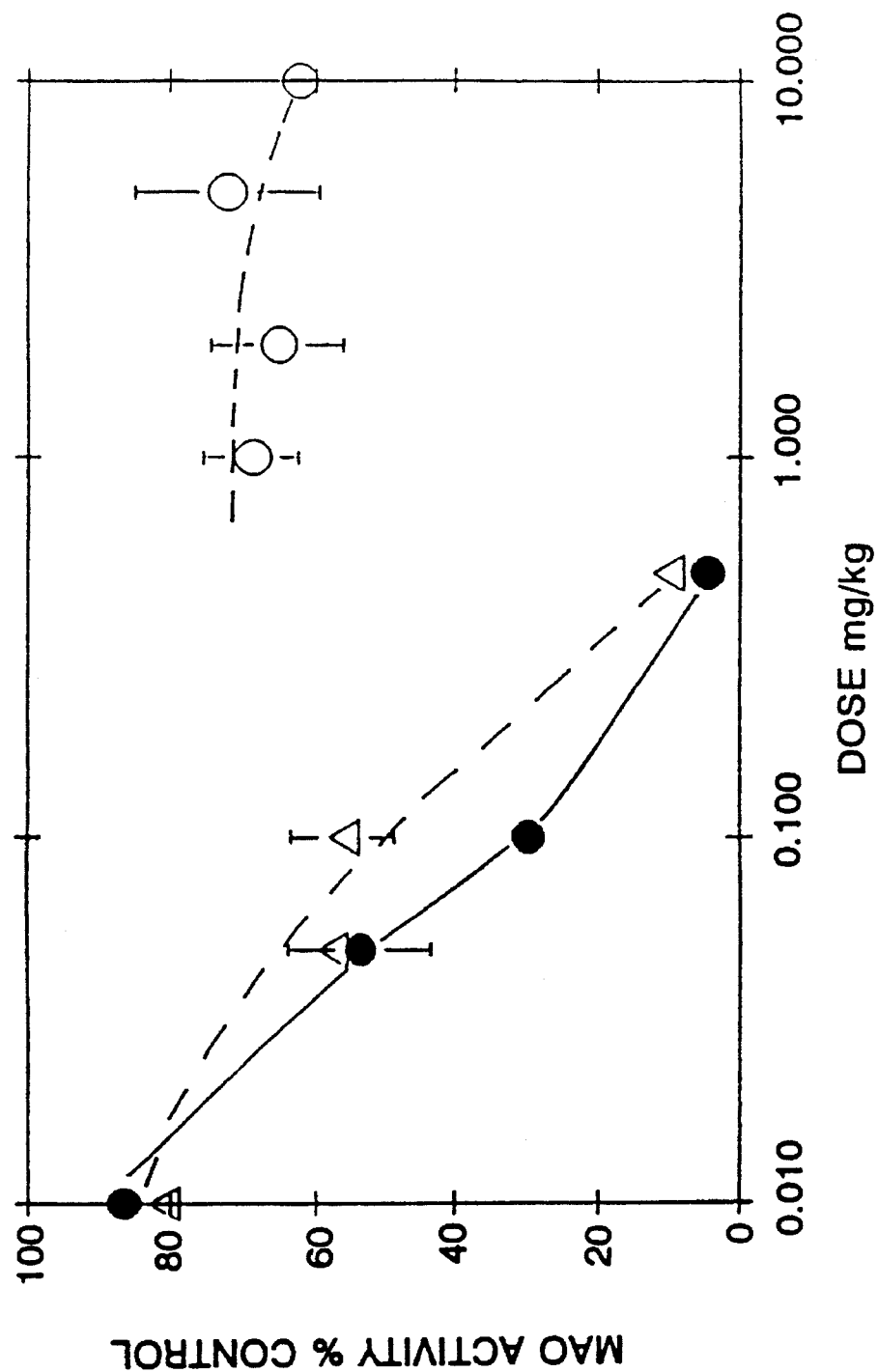
FIG. 11 is a graphic representation of the results according to Example 20.

Some experiments were also carried out with human cerebral cortical tissues, obtained 6 hours post-mortem, and treated as described above. The results of such an experiment are shown in FIG. 3 (where the R(+)PAI, S(−)PAI and racemic PAI compounds were those equivalent to formula I).

EXAMPLE 20

Inhibition of MAO activity in vivo: acute treatment
Experimental protocol:

Rats (male Sprague-Dawley derived) weighing 250±20 g were treated with one of the enantiomers or the racemic form of PAI by intraperitoneal injection (ip) or oral gavage (po) and decapitated 1 h or 2 h later respectively. Groups of three rats were used for each dose level of inhibitor, and MAO activity determined in brain and liver using the general technique described above. The amount of protein in each incubation was determined using the Folin-Lowry method, and enzyme activity calculated as nmol substrate metabolized per hour incubation for each mg protein. Activity of MAO in tissues from animals treated with inhibitors was expressed as a percentage of the enzyme activity in a group of control animals, administered vehicle (water for oral administration; 0.9% saline for ip injection) and killed as above.

Results:

None of the dose levels used with the inhibitor drugs produced any obvious behavioural alteration. The results are depicted in FIGS. 4 to 11. Following ip administration, compound R(+)-PAI produced 90% inhibition of brain MAO-B activity at a dose of 0.5 mg/kg. The same dose produced only 20% inhibition of MAO-A activity. By oral administration, the same dose of R(+)-PAI produced 80% inhibition of MAO-B with no detectable inhibition of MAO-A. Essentially similar results were seen for inhibition of hepatic MAO, as for brain MAO. The doses producing 50% inhibition of MAO-A and MAO-B (IC-50) were calculated from the inhibition curves, and are shown in Table 2. These data show:

(a) that MAO inhibitory activity of compound R(+)-PAI is maintained in vivo in the rat;

(b) that selectivity for inhibition of MAO-B, as opposed to MAO-A, by R(+)-PAI is maintained in vivo;

(c) that the much greater activity of the (+)-as opposed to (−)-enantiomer, is maintained in vivo;

(d) that the compounds are effectively absorbed after oral administration; and (e) that the compounds effectively pass the blood-brain barrier, and effectively inhibit brain MAO. The fact that R(+)-PAI was about twice as active as the racemic compound for inhibition of MAO-B is a reflection of the extremely low activity of S(−)-PAI for inhibition of MAO-B.

TABLE 2

IC-50 VALUES (mg/kg) FOR INHIBITION OF MAO-A AND MAO-B BY R(+)-PAI, S(−)-PAI OR RACEMIC-PAI, IN THE RAT FOLLOWING INTRAPERITONEAL (IP) INJECTION OR ORAL ADMINISTRATION (PO)

| | IC-50 (mg/kg) | | | | | |
|---|---|---|---|---|---|---|
| Com- | MAO-A | | | MAO-B | | |
| pound: | S(−)PAI | R(+)PAI | Rac | S(−)PAI | R(+)PAI | Rac |
| IP BRAIN | >10 | 1.2 | 2.5 | >10 | 0.07 | 0.22 |
| IP LIVER | >10 | 5 | 5 | >10 | 0.06 | 0.11 |
| PO BRAIN | >10 | >5 | >5 | >10 | 0.17 | 0.29 |
| PO LIVER | >10 | >5 | >5 | >10 | 0.05 | 0.09 |

EXAMPLE 21

Inhibition of MAO activity in vivo: chronic treatment
Experimental protocol:

Rats (specification as in Example 20:4 animals for each dose level) were treated with compound R(+)-PAI or racemic form at three dose levels (0.05, 0.1 and 0.5 mg/kg) by oral administration, one dose daily for 21 days, and decapitated 2 hours after the last dose. The activity of MAO types A and B was determined in brain and liver as described in Example 20.

Figure 12:
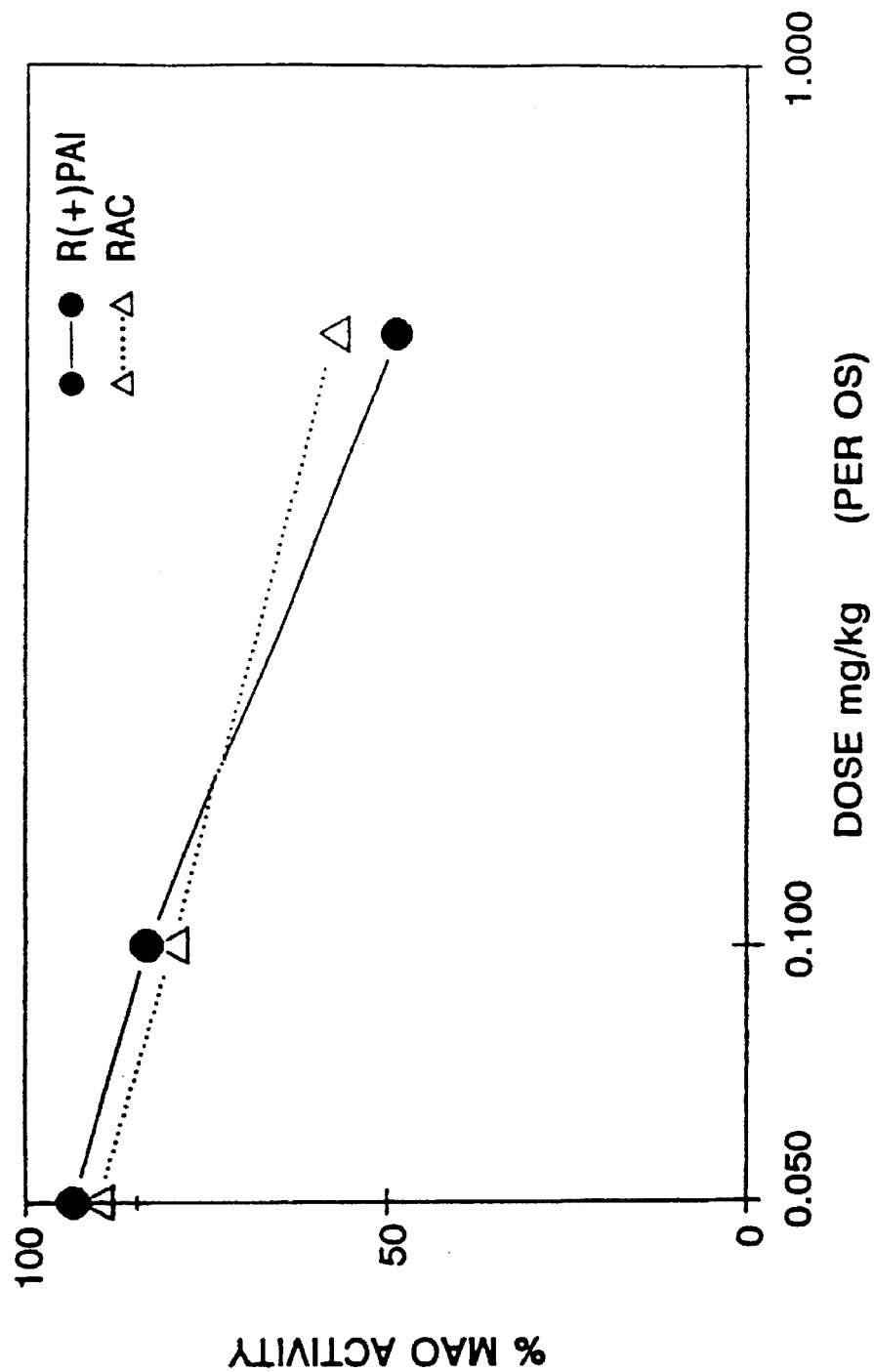
FIG. 12 is a graphic representation of the results according to Example 21.
Figure 13:
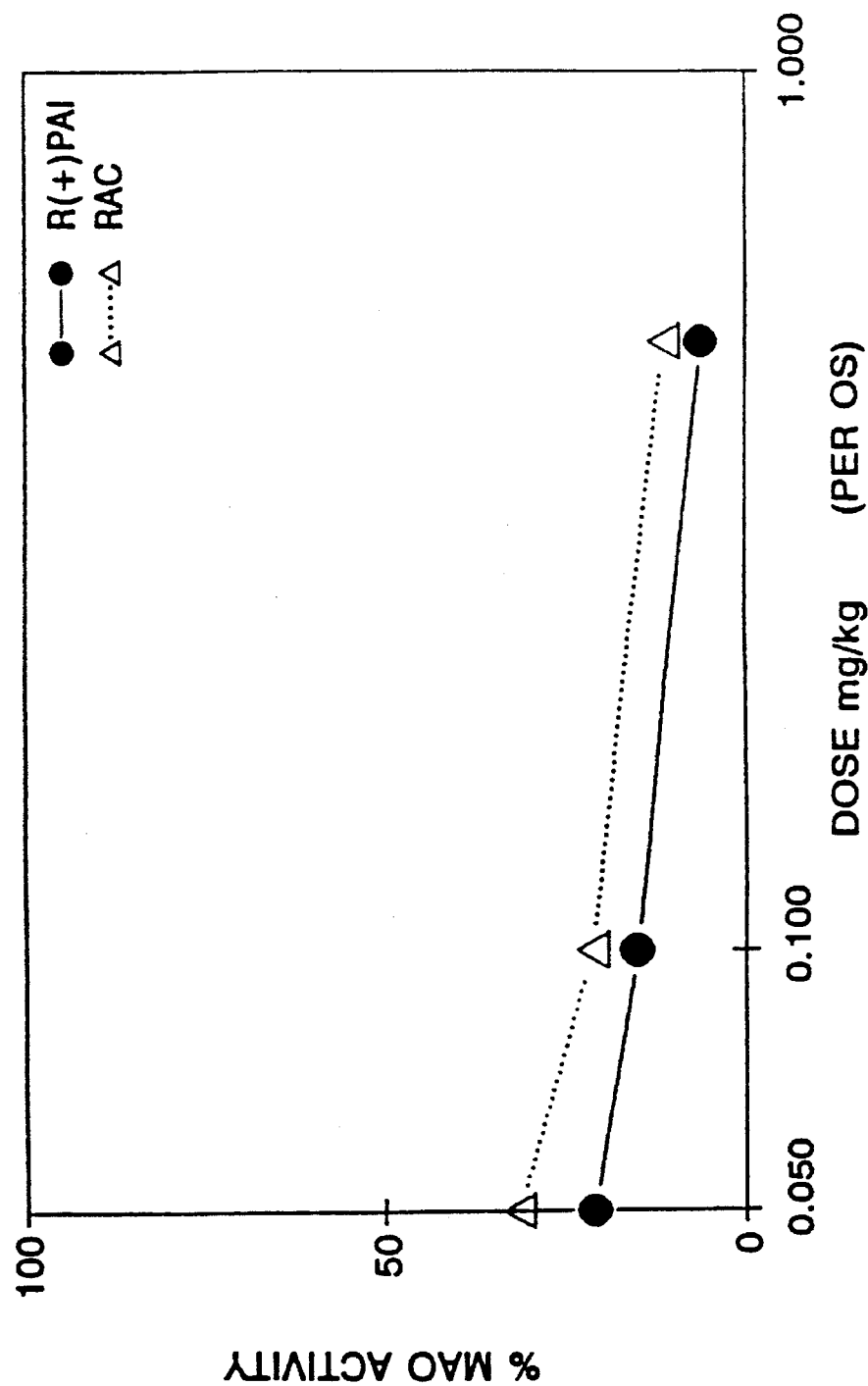
FIG. 13 is a graphic representation of the results according to Example 21.
Figure 14:
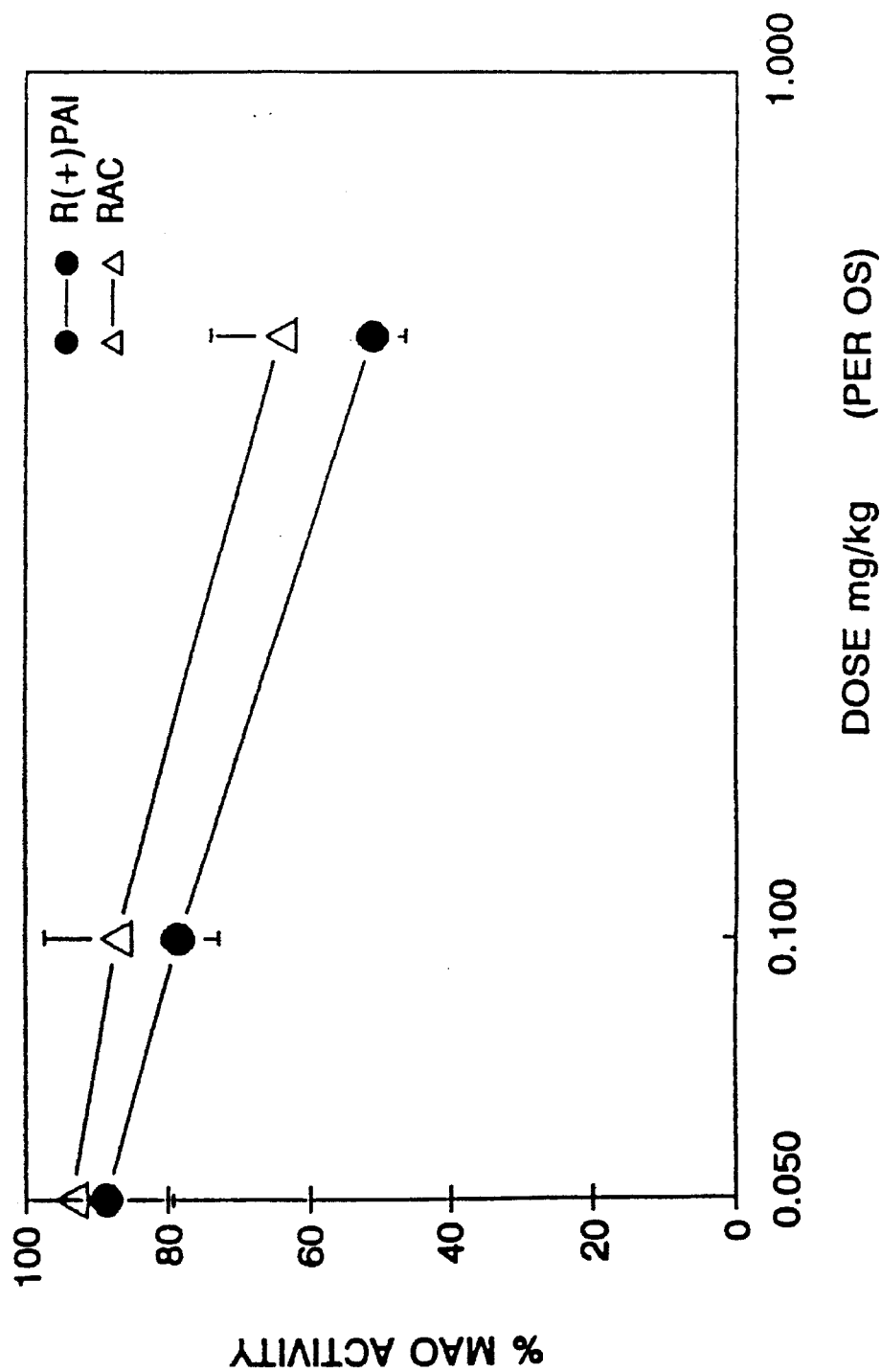
FIG. 14 is a graphic representation of the results according to Example 21.
Figure 15:
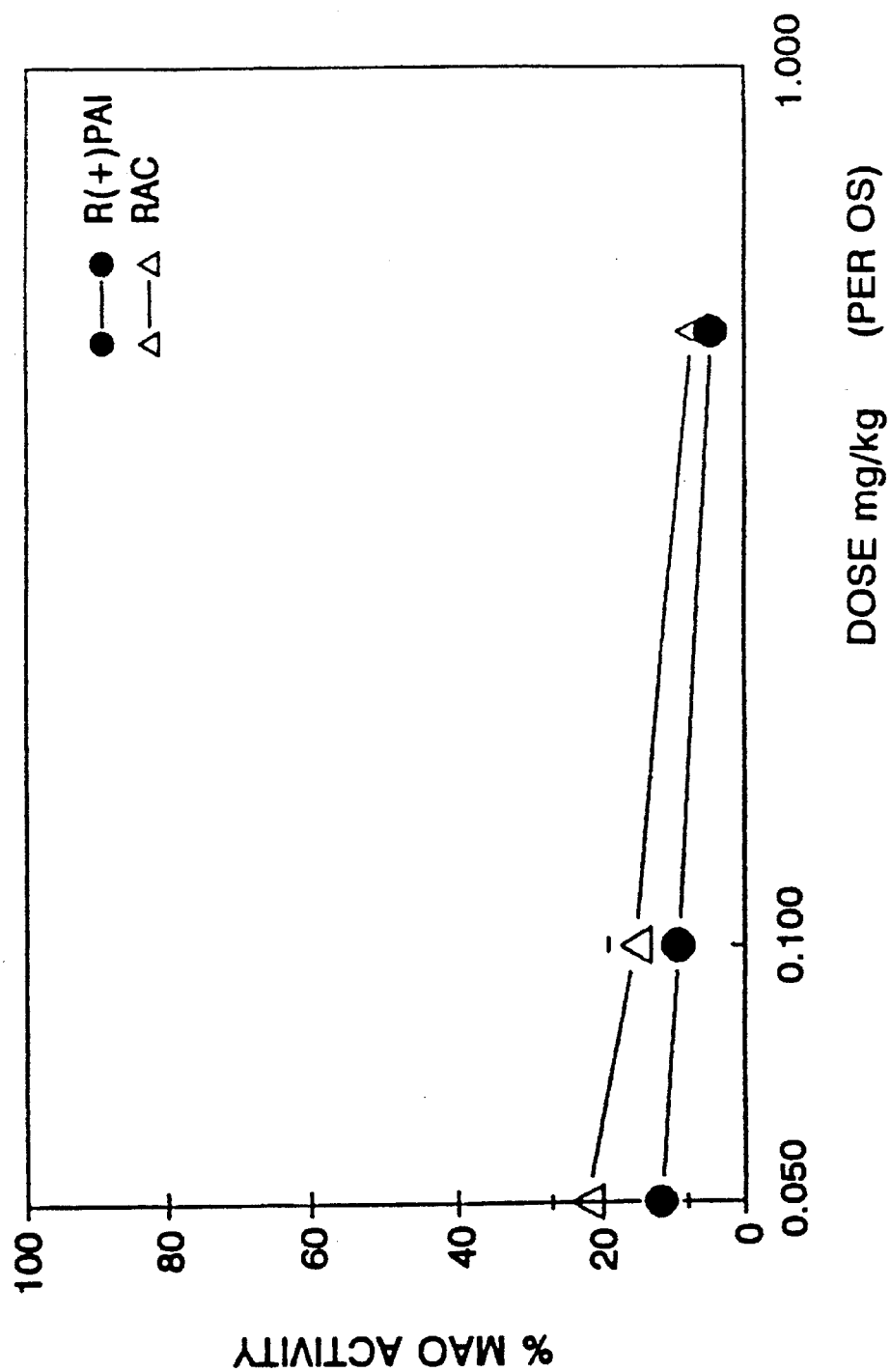
FIG. 15 is a graphic representation of the results according to Example 21.

Results:

A dose of 0.1 mg/kg daily of compound R(+)-PAI produced a good degree of selective inhibition, with more than 80% inhibition of brain MAO-B and 20% or less inhibition of brain MAO-A. At the higher dose of 0.5 mg/kg daily, MAO-A was still inhibited by less than 50% (FIGS. 12 and 13). Hepatic MAO showed a similar degree of selective inhibition (FIGS. 14 and 15). Compound R(+)-PAI was again more potent than the racemic form of the inhibitor, by a factor of about twofold. In the case of brain MAO, R(+)-PAI had a better degree of selectivity for inhibition of MAO-B than the racemic form.

These results show that selectivity of MAO-B inhibition can be maintained following chronic treatment with the compounds. As with other irreversible inhibitors, the degree of enzyme inhibition is greater with chronic treatments than following a single dose of the drug. Compound R(+)-PAI shows a better degree of selectivity for inhibition of brain MAO-B than the racemic compound.

EXAMPLE 22

Irreversible nature of MAO inhibition
Experimental protocol:

A single dose of compound R(+)-PAI (1 mg/kg) was administered by ip injection to groups of 4 rats, and the animals killed 2,6,18,24,48 and 72 hours later. Activity of MAO-B was determined in whole brain tissues as described herein before.

Figure 16:
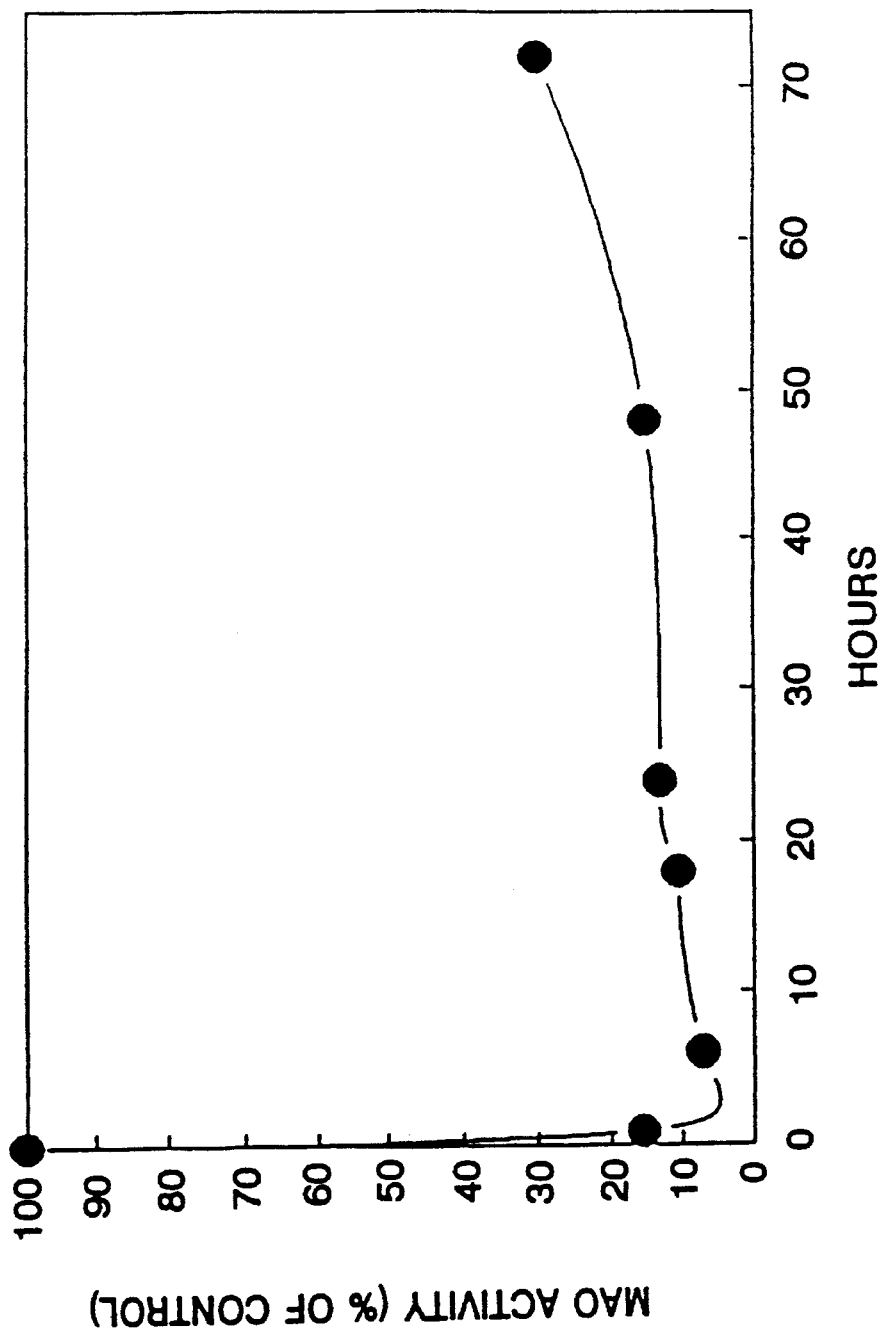
FIG. 16 is a graphic representation of the results according to Example 22.

Results:

The results are shown in FIG. 16. Maximal inhibition of MAO-B was attained at 6 hours after the injection. MAO activity had only returned to 30% control activity at 72 hours after the injection. This experiment demonstrates the irreversible nature of the MAO inhibition by compound R(+)-PAI.

EXAMPLE 23

Potentiation of tyramine pressor effect in conscious rats
Experimental protocol:

Rats were anesthetised with a mixture of pentobarbital (30 mg/kg) and chloral hydrate (120 mg/kg) by intraperitoneal injection. The left carotid artery and jugular vein were cannulated with fine polythene tubing (artery) or fine silicone rubber tubing connected to polyethylene tubing (vein), the distal end of which was brought under the skin to an anchor point behind the neck. The tubing was filled with heparinised saline solution, and plugged with a fine steel rod. The animals were treated with 20 mg chloramphenicol by intramuscular injection and allowed to recover from the operation overnight. The following day, the rats were placed in a high-walled container permitting free movement. The arterial catheter was connected to a pressure transducer via a 100 cm length of saline-filled, fine-bore polyethylene tubing, and the venous catheter connected to a 1 ml syringe via a similar length of tubing, which, together with the syringe, contained a solution of tyramine hydrochloride in saline (1 mg/ml).

Following an equilibration period of 30 to 40 min, tyramine injections (50 or 100 g) were given, and blood pressure responses recorded. At least 15 min was maintained between injections, after return of blood pressure to control values. Control pressor responses were established, and then one of the drugs injected intra-peritoneally, and tyramine responses repeated over the next 4 hours. Area under the blood pressure response curve was estimated, and the ratio of this area after treatment to before treatment determined, using the average off 3 to 4 values obtained in control period, and 1 to 3 hours after injection of the compounds.

Results:

The results are shown in Table 3. Compound R(+)-PAI at a dose of 1 mg/kg, (which causes complete inhibition of MAO-B in brain and liver, and 40 to 50% inhibition of MAO-A in these tissues) caused no significant potentiation of tyramine pressor response. At the higher R(+)-PAI dose of 5 mg/kg, (which causes more extensive inhibition of MAO-A in brain and periphery), there was a significant potentiation of the tyramine pressor response, which was similar in extent to that produced by the same dose of deprenyl, and less than that produced by clorgyline (at a dose which inhibits hepatic MAO-A activity by over 85%).

TABLE 3

POTENTIATION OF TYRAMINE PRESSOR EFFECT IN CONSCIOUS RATS BY MAO INHIBITORS

| Inhibitor | Dose (mg/kg) | No. of rats (n) | Ratio Area Under Pressor Response Curve; After/Before | SEM |
|---|---|---|---|---|
| Saline | | 12 | 1.25 | 0.28 |
| Clorgyline | 2 | 6 | 10.39 | 2.13 |
| (−)Deprenyl | 1 | 2 | 1.15 | |
| (−)Deprenyl | 5 | 3 | 2.36 | 0.16 |
| R(+)PAI | 1 | 3 | 1.38 | 0.7 |
| R(+)PAI | 5 | 3 | 3.49 | 0.98 |

From this experiment it can be concluded that compound R(+)-PAI causes no potentiation of the tyramine pressor effect at a dose which effectively inhibits MAO-B.

EXAMPLE 24

Suppression of MPTP-Induced dopaminergic Toxicity by R(+)-PAI

1-Methyl-4-phenyl-1,2,3,6-tetrahydropyridine (MPTP) is a neurotoxin that damages nigrostriatal dopaminergic neurons in several mammalian species including mice and produces a parkinsonian syndrome in humans and primates. A crucial initial step in the mechanism of its neurotoxicity involves conversion of MPTP to its toxic metabolite 1-methyl-4-phenyl pyridinium ion (MPP+). This reaction is catalyzed by the enzyme MAO-B and probably takes place outside of dopaminergic neurons, mainly in glia. It is known that MPTP is both a substrate and an irreversible inhibitor of MAO-B. Pretreatment of experimental animals with MAO-B inhibitors such as deprenyl or pargyline protects against and prevents the MPTP-induced damage to nigrostriatal neurons because the oxidative conversion of MPTP to MPP+ is blocked. One of the major current hypotheses suggests that the progressive nigrostriatal degeneration in Parkinson's may be due to exposure to environmentally-derived exogenous MPTP-like neurotoxins. In such case, there is an additional strong indication to initiation of sustained treatment with an MAO-B inhibitor from the very early stages of Parkinson's disease in the hope that it will neutralize the damaging effects of such yet putative MPTP-like toxins and thus arrest or slow down the progression of the illness. A successful MAO-B inhibitor drug is currently judged by its ability to block MPTP-induced damage to nigrostriatal dopaminergic neurons in vivo. We therefore tested the (−) and (+) enantiomers of PAI for their potency in preventing or attenuating the MPTP-induced striatal dopamine depletions in mice.

Experimental Protocol:

Male C57 black mice (20–25 g weight) were injected with MPTP.HCl (30 mg/kg dissolved in distilled water, s.c.) or vehicle alone or one hour after pretreatment with the (−) or (+) isomers of PAI (2.5 mg/kg, i.p.) or with deprenyl (5 mg/kg, i.p.) and decapitated 5 days later. Brains were removed and corpora striata dissected on an ice-cold glass plate and frozen on dry ice. Striatal tissues were homogenized in 0.1M perchloric acid, and deproteinized aliquots containing dihydroxybenzylamine as an internal standard were assayed for dopamine and its major metabolite 3,4-dihydroxy-phenylacetic acid (DOPAC) using HPLC with electro-chemical detection.

Results:

Table 4 shows the results of this experiment. Treatment with MPTP alone produced marked striatal dopamine (DA) and DOPAC depletions. Treatment with the (−) and (+) enantiomers of PAI or with (−) deprenyl did not affect striatal DA concentrations. Pretreatment with the (−) isomer of PAI did not affect the MPTP-induced DA and DOPAC levels in striatum. The (+)-isomer of PAI given before MPTP, completely abolished the reduction in striatal DA and DOPAC levels produced by the toxin. At a dose of 2.5 mg/kg it was equipotent to (−) deprenyl (5 mg/kg) in its protective effect.

TABLE 4

EFFECT OF PRETREATMENT WITH THE (−) AND (+) ENANTIOMERS OF THE MAO-B INHIBITOR PAI ON THE STRIATAL DA AND DOPAC DEPLETIONS INDUCED BY MPTP IN MICE IN VIVO.

| | DA | DOPAC |
|---|---|---|
| | (ng/mg protein) | |
| Control | 162.8 ± 7.2 | 8.4 ± 0.5 |
| MPTP | 53.1 ± 6.2 | 3.2 ± 0.3 |
| (−)-PAI | 174.0 ± 4.8 | 7.5 ± 0.2 |
| (−)-PAI + MPTP | 53.4 ± 6.9 | 7.0 ± 0.6 |
| (+)-PAI | 185.0 ± 6.9 | 3.3 ± 0.3 |
| (+)-PAI + MPTP | 177.8 ± 14.4 | 6.0 ± 0.3 |
| (−) Deprenyl | 170.6 ± 7.1 | 5.6 ± 0.3 |
| (−) Deprenyl + MPTP | 197.0 ± 8.0 | 6.4 ± 0.5 |

Above values for DA and DOPAC expressed as Mean ± S.E.M., and No. of rats, n = 7–11 in each group.

These results indicate that the R(+)-PAI is an excellent MAO-B inhibitor in vivo, and is of especially great potential for the treatment of Parkinson's disease.

While the invention has been described with reference to the aforementioned Examples and their accompanying Tables and Figures, it is not restricted thereto. Various modifications and applications of the invention are possible, for example, compounds of Formula I may be combined, in a synergistic way, with α-tocopherol (Vit. E. deriv.) for the treatment of Parkinson's disease.

EXAMPLE 25

Effect of PAI enantiomers on amphetamine induced stereotype behavior in senescent rats Amphetamine is known to induce stereotypic behaviour (Sulser, F. & Sanders-Bush, E. Ann. Rev. Pharmacol. 11: 209–230 (1971)) by the mobilization of endogenous dopamine. Amphetamine is not metabolized by MAO-B. Inhibition of MAO-B by an effective inhibitor and administration of amphetamine cause release of dopamine which will not undergo degradation by the inhibited MAO-B. Thus, an increase of synaptic dopamine is expected after administration of amphetamine and effective MAO-B inhibitor leading to an increase in stereotype behavior—potentiation of the amphetamine effect. The extent of this behaviour is rated in accordance with the number of lateral head movements over a period of 1 minute.

Experimental Protocol:

The test compound was administered at a dose of 0.5 mg/kg/day in drinking water, 24 hours before the infliction of hypoxia (92% nitrogen+8% oxygen for 6 hours). Following that, amphetamine was injected s.c. at a dose of 0.5 mg/kg 45 min. later, lateral head movements were counted.

Results:

The results of these experiments are shown in Table 5.

TABLE 5

EFFECT OF PAI ISOMERS ON AMPHETAMINE-INDUCED STEREOTYPE BEHAVIOUR IN SENESCENT RATS (CONTROL AND HYPOXIALESIONED)

| Group | Treatment | Stereotype Behavior Rating |
|---|---|---|
| Control (6) | — | 87 ± 10 |
| Control (5) | (+) PAI | 126 ± 16- |
| Control (4) | (−) PAI | 94 ± 18 |
| Hypoxia lesioned (5) | — | 93 ± 12 |

TABLE 5-continued

EFFECT OF PAI ISOMERS ON AMPHETAMINE-INDUCED STEREOTYPE BEHAVIOUR IN SENESCENT RATS (CONTROL AND HYPOXIALESIONED)

| Group | Treatment | Stereotype Behavior Rating |
|---|---|---|
| Hypoxia lesioned (6) | (+) PAI | 143 ± 6- |

Numbers in parenthesis are numbers of animals tested $P < 0.001$ with respect to untreated hypoxia group or untreated control group correspondingly The results in Table 5 indicate that (+)PAI caused significant potentiation of the amphetamine-induced stereotype behavior in both hypoxia-lesioned and control rats. (−)PAI was totally inactive in this respect. These behavioral in vivo results corroborate previous biochemical findings that (+)PAI is an active inhibitor of MAO-B in the brain while (−)PAI is inactive in this respect.

EXAMPLE 26

Effect on R(+)PAI on the improvement or restoration of memory

Newborn rat pups subjected to a brief episode of anoxia and then allowed to resume their growth in a normal way, develop a long-lasting impairment of memory (Speiser, et al., Behav. Brain Res. 30:89–94, 1988). This memory impairment is expressed as an inferior performance in the passive avoidance test.

The effect of R(+)PAI and S(−1)PAI on the improvement or restoration of memory was investigated in the passive avoidance test. If the drug is effective it increases the latency of response to enter a dark compartment or chamber where an electroshock has been experienced earlier by the rat being tested. The latency of the maximal response is 300 seconds.
Experimental Protocol:

Young rats were subjected to post-natal anoxia as described in Example 27. R(+)PAI or S(−)PAI were administered according to one of the following protocols:

Protocol A—Nursing mothers were given a dose of either isomer of 1–1.5 mg/kg/day, in drinking water until weaning at 21 days. Following that the weaned offsprings were directly dosed with the same dose for 20 days. Treatment was terminated at 40 days and the test was performed at 60 days, that is 20 days after the last dose of the drug.

Protocol B—The dose was reduced to 0.5 mg/kg/day administered to the nursing mother till weaning at 21 days than directly to the young rats to 60 days at which time the test was performed.

Passive Avoidance Test—The apparatus consisted of a lit chamber adjoining a dark chamber and a sliding door separating the two. At training, a rat was placed in the lit chamber for 30 sec. then the door was opened. The rat moved to the dark chamber with a latency that was recorded. Upon entry of the rat into the dark compartment, the door was closed and a 0.3 mA foot—shock was delivered for 3 sec.

Retention (memory) after 48 hours was determined by repeating the test and recording the latency to step through from light to darkness to an arbitrary maximum of 300 sec.
Results:

The results of these experiments are shown in Table 6.

TABLE 6

EFFECT OF PAI ISOMERS ON PASSIVE AVOIDANCE RESPONSE IN YOUNG RATS (60-DAYS OLD)

| Group | Treatment | Before Electroshock | After Electroshock |
|---|---|---|---|
| PROTOCOL A | | | |
| Control | — | 49 ± 13 | 201 ± 111 |
| Control | (+)PAI | 49 ± 19 | 220 ± 100(+9%)* |
| Control | (−)PAI | 48 ± 13 | 192 ± 116 |
| Anoxia-lesioned | — | 45 ± 11 | 183 ± 109 |
| Anoxia-lesioned | (+)PAI | 49 ± 10 | 239 ± 99(+19*)* |
| Anoxia-lesioned | (−)PAI | 55 ± 27 | 179 ± 123 |
| PROTOCOL B | | | |
| Control | — | 53 ± 20 | 104 ± 101 |
| Control | (+)PAI | 48 ± 11 | 128 ± 119(+23%)* |
| Anoxia-lesioned | — | 45 ± 8 | 119 ± 105 |
| Anoxia-lesioned | (+)PAI | 52 ± 12 | 137 ± 126(+15%)* |
| Anoxia-lesioned | (−)PAI | 48 ± 19 | 112 ± 112 |

— Figures represent the latency in seconds for entering a dark compartment where an electroshock had been first experienced by the rat tested.
*The indicated percent increases are with respect to the anoxia or control groups correspondingly.

The experimental results indicated that (+)PAI but not (−)PAI is effective in improving the memory of anoxia-lesioned and control rats. Drugs active in this test are considered to be potentially useful for treatment of various memory impairment disorders, dementia and especially senile dementia of the Alzheimer's type.

EXAMPLE 27

Effect of R(+)PAI on the anoxia-induced hyperactive syndrome in juvenile rats

Rats that had been exposed postnatally to anoxia and then left to grow under normal conditions show increased motor activity in the open field at the age of 10–42 days (Hertshkowitz et al., Dev. Brain Res. 7:145–155 (1983)).

The effect of R(+)PAI and R(−)PAI on such hyperactive syndrome was investigated.
Experimental Protocol:

Anoxia was performed on rat pups on the first post-natal day. They were placed in a glass chamber and exposed to 100% nitrogen for 25 min. They were resuscitated by intermittent massage softly applied to the chest and then returned to their respective mothers. Control rats received the same treatment but with air instead of nitrogen.

The R(+)PAI or S(−)PAI (0.5 mg/kg/day ) was administered to the nursing mothers in drinking water, thereby transferred to the sucklings through milk.

Locomotion was measured in 6 fully computerized cages (28×28 cm) by recording the number of crossing over a given period of time. Crossings of grid infrared beams at 4-cm intervals initiated electrical impulses which fed a counter. Recordings of motor activity were made at the ages of 15 and 20 days, over a period of 15 min.
Results:

The experimental results are given in Table 7.

TABLE 7

EFFECT OF EACH OF THE TWO ENANTIOMERS ON THE ANOXIA-INDUCED HYPERACTIVE SYNDROME

| Group | Treatment | 15-day old rats | 20-day old rats |
|---|---|---|---|
| Control | — | 414 ± 192(11) | 808 ± 212(12) |
| Control | (+)PAI | 254 ± 149(11)c | 719 ± 110(13) |

TABLE 7-continued

EFFECT OF EACH OF THE TWO ENANTIOMERS ON THE ANOXIA-INDUCED HYPERACTIVE SYNDROME

| Group | Treatment | 15-day old rats | 20-day old rats |
| --- | --- | --- | --- |
| Anoxia-lesioned | — | 482 ± 119 (7) | 858 ± 96 (9) |
| Anoxia-lesioned | (+)PAI | 276 ± 186(15)a | 737 ± 150(16)c |
| Anoxia-lesioned | (−)PAI | 334 ± 196 (5) | 778 ± 232 (6) |

Numbers in parenthesis are numbers of animals tested.
— The figures are the number of crossings of infrared beam grid in the activity cage over a period of 15 minutes.
a $P < 0.001$ compared to anoxia untreated group.
b $P < 0.05$ compared to anoxia untreated group.
c $P < 0.05$ compared to control group.

These results indicate that chronic oral treatment with R(+)PAI at dose of 0.5 mg/kg administered to the nursing mother and reaching the milk-fed offspring, significantly improved the hyperactive syndrome. Consequently, R(+)PAI is a potentially useful drug for the treatment of the hyperactive syndrome in children.

We claim:

1. A method of treating a subject for memory disorders which comprises administering to the subject an amount of R(+)-N-propargyl-1-aminoindan or a pharmaceutically acceptable salt thereof effective to treat the subject.

2. The method of claim 1, wherein the R(+)-N-propargyl-1-aminoindan or pharmaceutically acceptable salt thereof is administered orally or rectally.

3. The method of claim 2, wherein the amount administered is 2 to 20 mg per daily dosage unit.

4. The method of claim 3, wherein the amount administered is 5 to 10 mg per daily dosage unit.

5. The method of claim 1, wherein the R(+)-N-propargyl-1-aminoindan or pharmaceutically acceptable salt thereof is administered parenterally.

6. The method of claim 5, wherein the amount administered is 1 to 10 mg per mL per daily dosage unit.

7. The method of claim 6, wherein the amount administered is 2 to 5 mg per mL per daily dosage unit.

* * * * *